(12) United States Patent
Kim et al.

(10) Patent No.: US 6,214,852 B1
(45) Date of Patent: Apr. 10, 2001

(54) N-[5-[[[5-ALKYL-2-OXAZOLYL]METHYL]THIO]-2-THIAZOLYL]-CARBOXAMIDE INHIBITORS OF CYCLIN DEPENDENT KINASES

(75) Inventors: Kyoung S. Kim, North Brunswick; S. David Kimball, East Windsor, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/616,629

(22) Filed: Jul. 26, 2000

Related U.S. Application Data

(63) Continuation-in-part of application No. 09/464,511, filed on Dec. 15, 1999, which is a continuation-in-part of application No. 09/176,239, filed on Oct. 21, 1998, now Pat. No. 6,040,321.

(51) Int. Cl.[7] .................. A61K 31/425; C07D 417/12
(52) U.S. Cl. ............... 514/369; 514/342; 546/280; 548/185
(58) Field of Search ............... 548/185; 546/280; 514/369, 342

(56) References Cited

U.S. PATENT DOCUMENTS

| 4,254,260 | 3/1981 | Takaya ................... 544/27 |

FOREIGN PATENT DOCUMENTS

| 0082498 B1 | 11/1989 | (EP) . |
| 0625307 A1 | 11/1994 | (EP) . |
| 0412404 B1 | 1/1996 | (EP) . |
| WO 95/24403 | 9/1995 | (WO) . |
| WO 96/17850 | 6/1996 | (WO) . |
| WO 96/30370 | 10/1996 | (WO) . |
| WO 97/29111 | 8/1997 | (WO) . |
| WO 99/21845 | 5/1999 | (WO) . |
| WO 99/24416 | 5/1999 | (WO) . |
| WO 00/26202 | 5/2000 | (WO) . |

OTHER PUBLICATIONS

T. Ogino et al., "Discovery of FR1115092: A Novel Anti-nephritic Agent"; Bioorg. & Med. Chem. Lett. 8 (1998) 75–80.

K. Tsuji et al., "Synthesis and Effects of Novel Thiazole Derivatives Against Thrombocytopenia"; Bioorg. & Med. Chem. Lett. 8 (1998) 2473–2478.

Baddi et al., "Synthesis and Antimicrobial Activity of Some Ethyl–2–amino/acetamido–5–arylthiothiazole–4–carboxylates and their sulphones: An attempted synthesis of 2–amino/acetamido[1]benzothiopyrano[3,2–d]thiazol–9(H)–ones"; Indian J. Chem. 35B (1996) 233–237.

*Primary Examiner*—Robert Gerstl
(74) *Attorney, Agent, or Firm*—Rena Patel; Timothy J. Babcock

(57) ABSTRACT

The present invention describes compounds of formula I

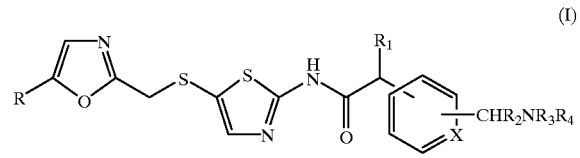

and enantiomers, diastereomers and pharmaceutically acceptable salts thereof.

The formula I compounds are protein kinase inhibitors and are useful in the treatment of proliferative diseases, for example, cancer, inflammation and arthritis. They may also be useful in the treatment of Alzheimer's disease, chemotherapy-induced alopecia, and cardiovascular disease.

38 Claims, No Drawings

N-[5-[[[5-ALKYL-2-OXAZOLYL]METHYL]THIO]-2-THIAZOLYL]-CARBOXAMIDE INHIBITORS OF CYCLIN DEPENDENT KINASES

RELATED APPLICATION

This application is a continuation-in-part of U.S. patent application Ser. No. 09/464,511, filed Dec. 15, 1999 which is a continuation-in-part of U.S. patent application Ser. No. 09/176,239, filed Oct. 21, 1998 now U.S. Pat. No. 6,040,321.

BRIEF DESCRIPTION OF THE INVENTION

The present invention is directed to compounds of formula I

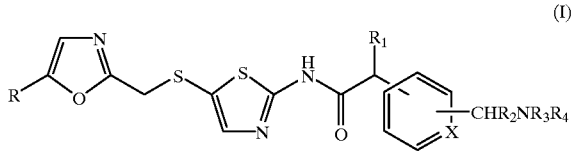

(I)

and enantiomers, diastereomers and pharmaceutically acceptable salts thereof wherein R is alkyl;

$R_1$ and $R_2$ are each independently hydrogen or alkyl;

$R_3$ is hydrogen or alkyl, and $R_4$ is hydrogen or alkyl substituted with one or two hydroxy groups or one $NR_5R_6$ group, or $R_3$ and $R_4$ are taken together with the nitrogen atom to which they are attached to form a 4- to 7-membered heterocyclic ring wherein $R_3R_4$ is represented by —$(CH_2)_n$— where n is an integer of 3, 4, 5 or 6;

$R_5$ and $R_6$ are each independently hydrogen, alkyl, substituted alkyl, cycloalkyl or substituted cycloalkyl, or $R_5$ and $R_6$ are taken together with the nitrogen atom to which they are attached to form a 4- to 7-membered heterocyclic ring wherein $R_5R_6$ is represented by —$(CH_2)_m$— where m is an integer of 3, 4, 5 or 6; and X is CH or N.

The compounds of formula I are particularly useful as potent, protein kinase inhibitors and are useful in the treatment of proliferative diseases, for example, cancer, inflammation and arthritis. They may also be useful in the treatment of Alzheimer's disease, chemotherapy-induced alopecia, and cardiovascular disease.

DESCRIPTION OF THE INVENTION

The present invention provides for compounds of formula I, pharmaceutical compositions employing such compounds, and for methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" or "alk" refers to a monovalent alkane (hydrocarbon) derived radical containing from 1 to 12, preferably 1 to 6, and more preferably 1 to 4, carbon atoms unless otherwise defined. An alkyl group is an optionally substituted straight, branched or cyclic saturated hydrocarbon group. When substituted, alkyl groups may be substituted with up to four substituent groups, $R_7$ as defined, at any available point of attachment. When the alkyl group is said to be substituted with an alkyl group, this is used interchangeably with "branched alkyl group". Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include, but are not limited to, one or more of the following groups: halo (such as F, Cl, Br or I), haloalkyl (such as $CCl_3$ or $CF_3$), alkoxy, alkylthio, hydroxy, carboxy, alkylcarbonyl, alkyloxycarbonyl, alkylcarbonyloxy, amino, carbamoyl, urea, amidinyl, or thiol.

Cycloalkyl is a specie of alkyl containing from 3 to 15 carbon atoms, without alternating or resonating double bonds between carbon atoms. It may contain from 1 to 4 rings. Exemplary unsubstituted such groups include cyclopropyl, cyclobutyl, cyclopentyl, cyclohexyl, etc. Exemplary substituents include one or more of the following groups: halogen, alkyl, alkoxy, alkyl hydroxy, amino, nitro, cyano, thiol and/or alkylthio.

The terms "alkoxy" or "alkylthio", as used herein, denote an alkyl group as described above bonded through an oxygen linkage (—O—) or a sulfur linkage (—S—), respectively.

The term "alkyloxycarbonyl", as used herein, denotes an alkoxy group bonded through a carbonyl group. An alkoxycarbonyl radical is represented by the formula: —$C(O)OR_8$, where the $R_8$ group is a straight or branched $C_{1-6}$ alkyl group.

The term "alkylcarbonyl" refers to an alkyl group bonded through a carbonyl group.

The term "alkylcarbonyloxy", as used herein, denotes an alkylcarbonyl group which is bonded through an oxygen linkage.

Pharmaceutically acceptable salts of the formula I compounds which are suitable for use in the methods and compositions of the present invention include, but are not limited to, salts formed with a variety of organic and inorganic acids such as hydrogen chloride, hydroxymethane sulfonic acid, hydrogen bromide, methanesulfonic acid, sulfuric acid, acetic acid, trifluoroacetic acid, maleic acid, benzenesulfonic acid, toluenesulfonic acid and various others, e.g., nitrates, phosphates, borates, tartrates, citrates, succinates, benzoates, ascorbates, salicylates, and the like. In addition, pharmaceutically acceptable salts of the formula I compounds may be formed with alkali metals such as sodium, potassium and lithium; alkaline earth metals such as calcium and magnesium; organic bases such as dicyclohexylamine, tributylamine, and pyridines, and the like; and amino acids such as arginine, lysine and the like.

All stereoisomers of the compounds of the instant invention are contemplated, either in admixture or in pure or substantially pure form. The definition of the compounds according to the invention embraces all possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

All configurational isomers of compounds of the present invention are contemplated, either in admixture or in pure or substantially pure form. The definition of compounds of the present invention very particularly embraces both cis and trans isomers of cycloalkyl rings.

It should be understood that solvates (e.g. hydrates) of the compounds of formula I are also within the scope of the present invention. Methods of solvation are generally known in the art. Accordingly, the compounds of the instant invention may be in the free or hydrate form, and may be obtained by methods exemplified by the following schemes.

Compounds of formula I may generally be prepared, as shown in Scheme 1, by reacting an amine of formula II with a carboxylic acid of formula III in the presence of a coupling reagent such as 1-(3-dimethylaminopropyl)-3-ethylcarbodiimide hydrochloride or 1,3-dicyclohexylcarbodiimide optionally in the presence of a base.

Scheme 1

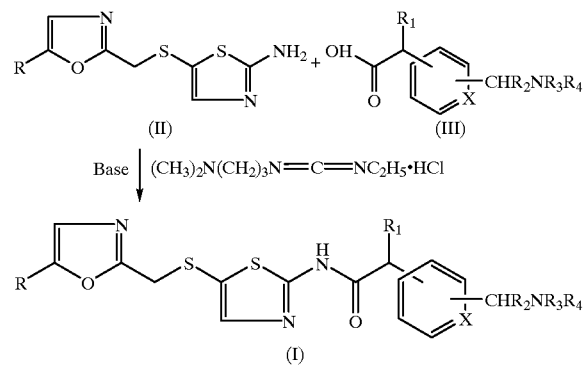

Formula I compounds may also be prepared, as shown in Scheme 2, by reacting an amine of formula II with a carboxylic acid of formula IV in the presence of a coupling reagent such as 1,3-dicyclohexylcarbodiimide or 1-(3-dimethylaminopropyl)-3-ethylcarbodiimide hydrochloride to form an intermediate compound of formula V, and reacting the intermediate compound with an amine of formula VI.

Scheme 2

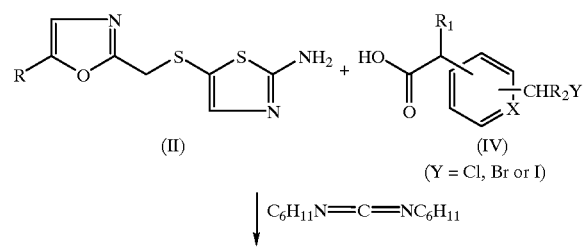

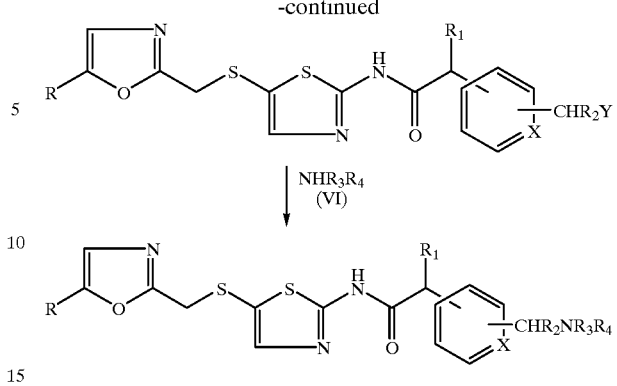

Compounds of formula I wherein $R_2$ is hydrogen may be prepared, as shown in Scheme 3, by reacting a carboxylic acid of formula VII with oxalyl chloride to form an acid chloride intermediate, reacting the acid chloride intermediate with an amine of formula II to form an aldehyde intermediate of formula VIII, and reacting the aldehyde intermediate with an amine of formula VI in the presence of a reducing agent such as sodium triacetoxyborohydride.

Scheme 3

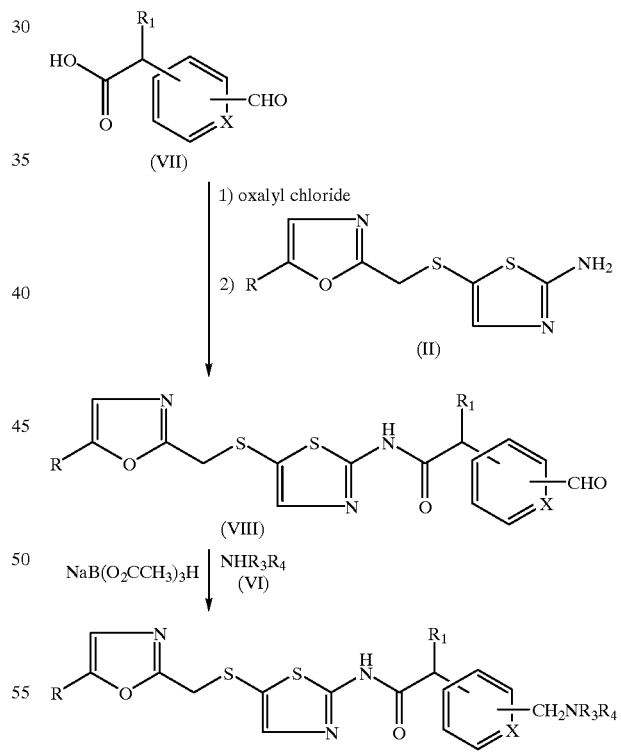

Formula I compounds wherein $R_2$ is alkyl may be prepared, as shown in Scheme 4, by reacting an aldehyde of formula VIII with an alkylmagnesium bromide of formula IX to form an alcohol of formula X, reacting the formula X alcohol with thionyl chloride to form a chloride of formula XI, and reacting the chloride compound with an amine of formula VI.

Scheme 4

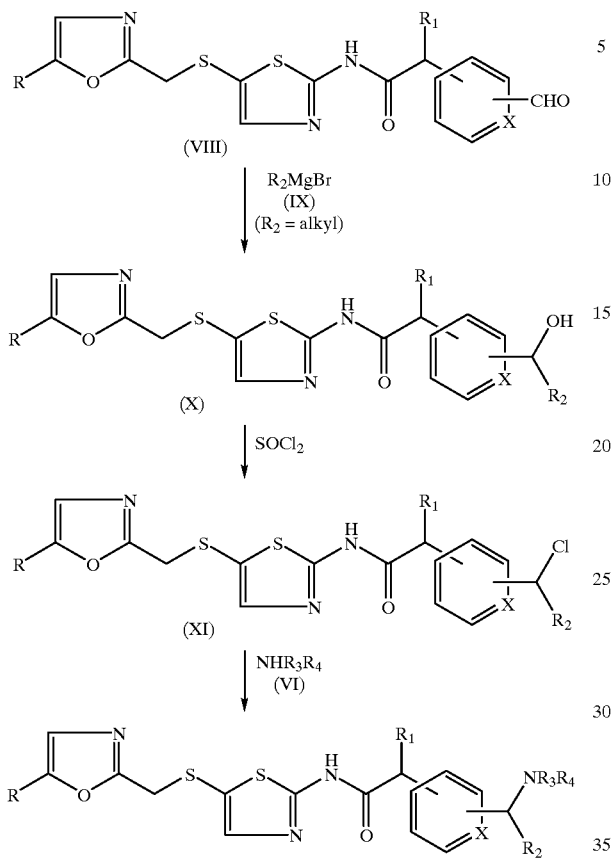

Furthermore, the examples provided herein describe additional methods for the preparation of the formula I compounds of the present invention.

Starting amines of formula II may be prepared as shown in Scheme 5. An alpha-bromoketone of formula XII may be reacted with sodium azide in a solvent such as dimethylformamide to provide the azido ketone derivative XIII, which is reduced by a reducing agent such as hydrogen in the presence of palladium on carbon catalyst, or triphenylphosphine to provide the amino ketone XIV. Compound XIV may alternatively be prepared by reaction of the alpha-bromoketone of formula XII with hexamethylenetetramine in a solvent such as acetone to give the compound of formula XV, which is hydrolyzed by an acidic medium such as hydrochloric acid in ethanol. Compounds of formula XIV may be acylated by an agent such as 2-chloroacetyl chloride to provide amides of formula XVI. The formula XVI amides are cyclized to 2-chloromethyl oxazoles of formula XVII using a dehydrating agent such as phosphorous oxychloride in toluene or Burgess' reagent in tetrahydrofuran. Reaction of the chloromethyl oxazoles of formula XVII with thiourea in a solvent such as ethanol provides the thiourea derivatives XVIII, which may be reacted with 5-bromo-2-aminothiazole in the presence of a base such as potassium hydroxide in alcohol to give formula II amines. Alternatively, reaction of the chloromethyl oxazole derivatives of formula XVII with 5-thiocyanato-2-aminothiazole, in the presence of a reducing agent such as sodium borohydride, provides compounds of formula II.

Scheme 5

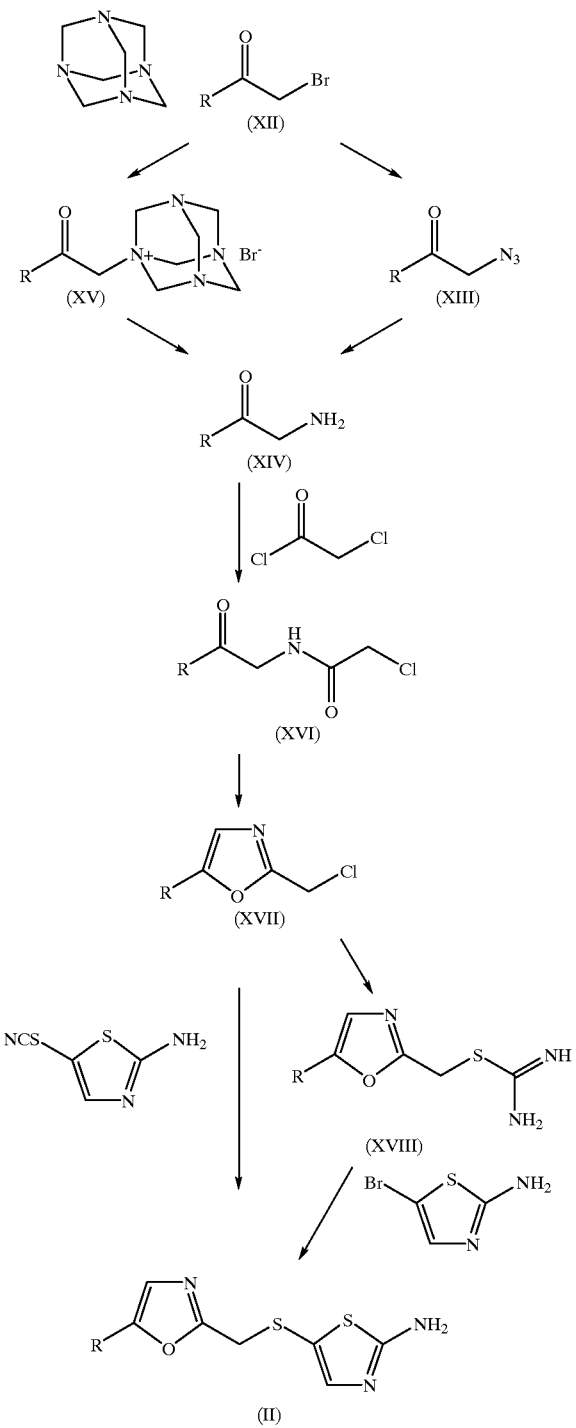

Preferred compounds of formula I are those wherein:

R is tert-butyl;

$R_1$ and $R_2$ are each independently hydrogen or methyl;

$R_3$ is hydrogen, and $R_4$ is hydrogen, —$CH_2C(CH_3)_2$ $CH_2OH$, —$CH_2CH_2OH$, —$C(CH_3)_2CH_2OH$, —CH $(CH_2OH)_2$, —$CH_2CH(OH)CH_2OH$, —$CH(CH_3)$ $CH_2OH$ or

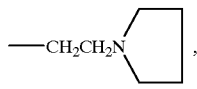

or $R_3$ and $R_4$ are taken together with the nitrogen atom to which they are attached to form a 5-membered heterocyclic ring where
$R_3R_4$ is represented by —$(CH_2)_4$—; and X is CH or N.

A first group of more preferred compounds of the present invention are those of formula Ia

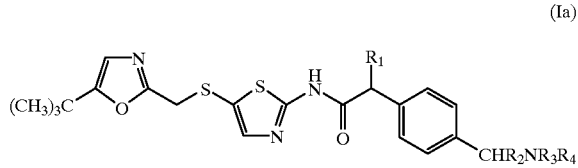

(Ia)

and enantiomers, diastereomers and pharmaceutically acceptable salts thereof wherein $R_1$ and $R_2$ are each independently hydrogen or methyl; and $R_3$ is hydrogen, and $R_4$ is hydrogen, —$CH_2C(CH_3)_2CH_2OH$, —$CH_2CH_2OH$, —$C(CH_3)_2CH_2OH$, —$CH(CH_2OH)_2$, —$CH_2CH(OH)CH_2OH$, —$CH(CH_3)CH_2OH$ or

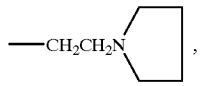

or $R_3$ and $R_4$ are taken together with the nitrogen atom to which they are attached to form a 5-membered heterocyclic ring
where $R_3R_4$ is represented by —$(CH_2)_4$—.

A second group of more preferred compounds of this invention are those of formula Ib

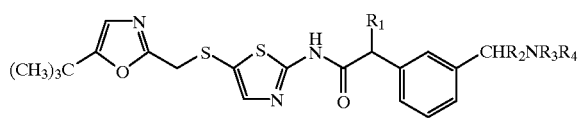

(Ib)

and enantiomers, diastereomers and pharmaceutically acceptable salts thereof wherein $R_1$ and $R_2$ are each independently hydrogen or methyl; and $R_3$ is hydrogen, and $R_4$ is hydrogen, —$CH_2C(CH_3)_2CH_2OH$, —$CH_2CH_2OH$, —$C(CH_3)_2CH_2OH$, —$CH(CH_2OH)_2$, —$CH_2CH(OH)CH_2OH$, —$CH(CH_3)CH_2OH$ or

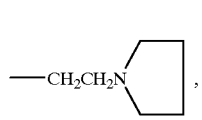

or $R_3$ and $R_4$ are taken together with the nitrogen atom to which they are attached to form a 5-membered heterocyclic ring
where $R_3R_4$ is represented by —$(CH_2)_4$—.

A third group of more preferred compounds of the present invention are those of formula Ic

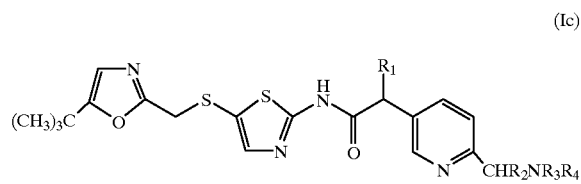

(Ic)

and enantiomers, diastereomers and pharmaceutically acceptable salts thereof wherein $R_1$ and $R_2$ are each independently hydrogen or methyl; and $R_3$ is hydrogen, and $R_4$ is hydrogen, —$CH_2C(CH_3)_2CH_2OH$, —$CH_2CH_2OH$, —$C(CH_3)_2CH_2OH$, —$CH(CH_2OH)_2$, —$CH_2CH(OH)CH_2OH$, —$CH(CH_3)CH_2OH$ or

or $R_3$ and $R_4$ are taken together with the nitrogen atom to which they are attached to form a 5-membered heterocyclic ring
where $R_3R_4$ is represented by —$(CH_2)_4$—.

A group of most preferred compounds of this invention are those of formulas Ia, Ib and Ic wherein $R_4$ is other than hydrogen.

Formula I compounds particularly useful in the methods of this invention include:

N-[5-[[[5-(1,1-dimethylethyl)-2-oxazolyl]methyl]thio]-2-thiazolyl]-4-[[[2-hydroxy-1-(hydroxymethyl)ethyl]amino]methyl]benzeneacetamide;

4-[[(2,3-dihydroxypropyl)amino]methyl]-N-[5-[[[5-(1,1-dimethylethyl)-2-oxazolyl]methyl]thio]-2-thiazolyl]benzeneacetamide;

(R)-4-[[(2,3-dihydroxypropyl)amino]methyl]-N-[5-[[[5-(1,1-dimethylethyl)-2-oxazolyl]methyl]thio]-2-thiazolyl]benzeneacetamide;

(S)-4-[[(2,3-dihydroxypropyl)amino]methyl]-N-[5-[[[5-(1,1-dimethylethyl)-2-oxazolyl]methyl]thio]-2-thiazolyl]benzeneacetamide;

4-(aminomethyl)-N-[5-[[[5-(1,1-dimethylethyl)-2-oxazolyl]methyl]thio]-2-thiazolyl]benzeneacetamide;

N-[5-[[[5-(1,1-dimethylethyl)-2-oxazolyl]methyl]thio]-2-thiazolyl]-4-[[(3-hydroxy-2,2-dimethylpropyl)amino]methyl]benzeneacetamide;

N-[5-[[[5-(1,1-dimethylethyl)-2-oxazolyl]methyl]thio]-2-thiazolyl]-4-(1-pyrrolidinylmethyl)benzeneacetamide;

N-[5-[[[5-(1,1-dimethylethyl)-2-oxazolyl]methyl]thio]-2-thiazolyl]-4-[[(2-hydroxyethyl)amino]methyl]benzeneacetamide;

N-[5-[[[5-(1,1-dimethylethyl)-2-oxazolyl]methyl]thio]-2-thiazolyl]-4-[[[2-(1-pyrrolidinyl)ethyl]amino]methyl]benzeneacetamide;

N-[5-[[[5-(1,1-dimethylethyl)-2-oxazolyl]methyl]thio]-2-thiazolyl]-4-[[(2-hydroxy-1,1-dimethylethyl)amino]methyl]benzeneacetamide;

N-[5-[[[5-(1,1-dimethylethyl)-2-oxazolyl]methyl]thio]-2-thiazolyl]-3-[[(2-hydroxyethyl)amino]methyl]benzeneacetamide;

N-[5-[[[5-(1,1-dimethylethyl)-2-oxazolyl]methyl]thio]-2-thiazolyl]-3-[[(3-hydroxy-2,2-dimethylpropyl)amino]methyl]benzeneacetamide;

3-(aminomethyl)-N-[5-[[[5-(1,1-dimethylethyl)-2-oxazolyl]methyl]thio]-2-thiazolyl]benzeneacetamide;

N-[5-[[[5-(1,1-dimethylethyl)-2-oxazolyl]methyl]thio]-2-thiazolyl]-4-[[(2-hydroxy-1-methylethyl)amino]methyl]benzeneacetamide;

N-[5-[[[5-(1,1-dimethylethyl)-2-oxazolyl]methyl]thio]-2-thiazolyl]-4-[1-[(2-hydroxyethyl)amino]ethyl]benzeneacetamide;

N-[5-[[[5-(1,1-dimethylethyl)-2-oxazolyl]methyl]thio]-2-thiazolyl]-4-[1-[(2-hydroxy-1-methylethyl)amino]ethyl]benzeneacetamide;

($\alpha$S)-N-[5-[[[5-(1,1-dimethylethyl)-2-oxazolyl]methyl]thio]-2-thiazolyl]-4-[[(2-hydroxyethyl)amino]methyl]-$\alpha$-methylbenzeneacetamide;

N-[5-[[[5-(1,1-dimethylethyl)-2-oxazolyl]methyl]thio]-2-thiazolyl]-6-[[(2-hydroxyethyl)amino]methyl]-3-pyridineacetamide; and N-[5-[[[5-(1,1-dimethylethyl)-2-oxazolyl]methyl]thio]-2-thiazolyl]-4-[[(2-hydroxyethyl)amino]methyl]-$\alpha$-methylbenzeneacetamide; and pharmaceutically acceptable salts thereof.

The compounds according to the invention have pharmacological properties;

in particular, the compounds of formula I are inhibitors of protein kinases such as the cyclin dependent kinases (cdks), for example, cdc2 (cdk1), cdk2, cdk3, cdk4, cdk5, cdk6, cdk7 and cdk8. The novel compounds of formula I are expected to be useful in the therapy of proliferative diseases such as cancer, inflammation, arthritis, Alzheimer's disease and cardiovascular disease. These compounds may also be useful in the treatment of topical and systemic fungal infections.

More specifically, the compounds of formula I are useful in the treatment of a variety of cancers, including (but not limited to) the following:

carcinoma, including that of the bladder, breast, colon, kidney, liver, lung, ovary, pancreas, stomach, cervix, thyroid, prostate, and skin;

hematopoietic tumors of lymphoid lineage, including acute lymphocytic leukemia, B-cell lymphoma, and Burkett's lymphoma;

hematopoietic tumors of myeloid lineage, including acute and chronic myelogenous leukemias and promyelocytic leukemia;

tumors of mesenchymal origin, including fibrosarcoma and rhabdomyosarcoma; and other tumors, including melanoma, seminoma, teratocarcinoma, osteosarcoma, neuroblastoma and glioma.

Due to the key role of cdks in the regulation of cellular proliferation in general, inhibitors could act as reversible cytostatic agents which may be useful in the treatment of any disease process which features abnormal cellular proliferation, e.g., neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, angiogenesis, and endotoxic shock.

Compounds of formula I may also be useful in the treatment of Alzheimer's disease, as suggested by the recent finding that cdk5 is involved in the phosphorylation of tau protein (*J. Biochem*, 117, 741–749 (1995)).

Compounds of formula I may also act as inhibitors of other protein kinases, e.g., protein kinase C, her2, raf1, MEK1, MAP kinase, EGF receptor, PDGF receptor, IGF receptor, PI3 kinase, wee1 kinase, Src, Abl, VEGF, and lck, and thus be effective in the treatment of diseases associated with other protein kinases.

Compounds of formula I also induce or inhibit apoptosis, a physiological cell death process critical for normal development and homeostasis. Alterations of apoptotic pathways contribute to the pathogenesis of a variety of human diseases. Compounds of formula I, as modulators of apoptosis, will be useful in the treatment of a variety of human diseases with abberations in apoptosis including cancer (particularly, but not limited to, follicular lymphomas, carcinomas with p53 mutations, hormone dependent tumors of the breast, prostate and ovary, and precancerous lesions such as familial adenomatous polyposis), viral infections (including, but not limited to, herpesvirus, poxvirus, Epstein-Barr virus, Sindbis virus and adenovirus), autoimmune diseases (including, but not limited to, systemic lupus, erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and aplastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

In addition, the formula I compounds may be used for treating chemotherapy-induced alopecia, chemotherapy-induced thrombocytopenia, chemotherapy-induced leukopenia or mucocitis. In the treatment of chemotherapy-induced alopecia, the formula I compound is preferably topically applied in the form of a medicament such as a gel, solution, dispersion or paste.

The compounds of this invention may be used in combination with known anti-cancer treatments such as radiation therapy or with cytostatic and cytotoxic agents including, but not limited to, microtuble-stabilizing agents, microtuble-disruptor agents, alkylating agents, anti-metabolites, epidophyllotoxin, an antineoplastic enzyme, a topoisomerase inhibitor, procarbazine, mitoxantrone, platinum coordination complexes, biological response modifiers, growth inhibitors, hormonal/anti-hormonal therapeutic agents, haematopoietic growth factors, and the like.

Classes of anti-cancer agents which may be used in combination with the formula I compounds of this invention include, but are not limited to, the anthracycline family of drugs, the vinca drugs, the mitomycins, the bleomycins, the cytotoxic nucleosides, the taxanes, the epothilones, discodermolide, the pteridine family of drugs, diynenes, aromatase inhibitors, and the podophyllotoxins. Particular members of those classes include, for example, paclitaxel, docetaxel, 7-O-methylthiomethylpaclitaxel (disclosed in U.S. Pat. No. 5,646,176), 3'-tert-butyl-3'-N-tert-butyloxycarbonyl-4-deacetyl-3'-dephenyl-3'-N-debenzoyl-4-O-methoxycarbonylpaclitaxel (disclosed in U.S. Ser. No. 60/179,965) filed on Feb. 3, 2000 which is incorporated herein by reference thereto), C-4 methyl carbonate paclitaxel (disclosed in WO 94/14787), epothilone A, epothilone B, epothilone C, epothilone D, desoxyepothilone A, desoxyepothilone B, [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4,17-dioxabicyclo[14.1.0]heptadecane-5,9-dione (disclosed in U.S. Ser. No. 09/506,481 filed on Feb. 17, 2000 which is incorporated herein by reference thereto), doxorubicin, carminomycin, daunorubicin, aminopterin, methotrexate, methopterin, dichloro-methotrexate, mitomycin C, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, leurosine, and the like. Other useful anti-cancer agents which may be used in combination with the compounds of the present invention include, but are not limited to, estramustine, cisplatin, carboplatin, cyclophosphamide, bleomycin, tamoxifen, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons, interleukins, and the like. In addition, the compounds of this invention may be used in combination with inhibitors of farnesyl protein transferase such as those described in U.S. Pat. No. 6,011,029; anti-angiogenic agents such as angiostatin and endostatin; kinase inhibitors such as her2 specific antibodies; and modulators of p53 transactivation.

If formulated as a fixed dose, such combination products employ the compounds of this invention within the dosage range described below and the other pharmaceutically active agent within its approved dosage range. Compounds of formula I may be used sequentially, in any order, with known anti-cancer or cytotoxic agents when a combination formulation is inappropriate.

The present invention also provides pharmaceutical compositions which comprise a compound of this invention and a pharmaceutically acceptable carrier. The compositions of the present invention may further comprise one or more pharmaceutically acceptable additional ingredient(s) such as alum, stabilizers, antimicrobial agents, buffers, coloring agents, flavoring agents, and the like. The compounds and compositions of this invention may be administered orally or parenterally including the intravenous, intramuscular, intraperitoneal, subcutaneous, rectal and topical routes of administration.

For oral use, the compounds and compositions of this invention may be administered, for example, in the form of tablets or capsules, or as solutions or suspensions. In the case of tablets for oral use, carriers which are commonly used include lactose and corn starch, and lubricating agents such as magnesium stearate are commonly added. For oral administration in capsule form, useful carriers include lactose and corn starch. When aqueous suspensions are used for oral administration, emulsifying and/or suspending agents are commonly added. In addition, sweetening and/or flavoring agents may be added to the oral compositions. For intramuscular, intraperitoneal, subcutaneous and intravenous use, sterile solutions of the active ingredient(s) are usually employed, and the pH of the solutions should be suitably adjusted and buffered. For intravenous use, the total concentration of the solute(s) should be controlled in order to render the preparation isotonic.

Daily dosages for human administration of the compounds of this invention will normally be determined by the prescribing physician with the dosages generally varying according to the age, weight, route of administration, and response of the individual patient, as well as the severity of the patient's symptoms. A formula I compound of this invention is preferably administered to humans in an amount from about 0.001 mg/kg of body weight to about 100 mg/kg of body weight per day, more preferably from about 0.01 mg/kg of body weight to about 50 mg/kg of body weight per day, and most preferably from about 0.1 mg/kg of body weight to about 20 mg/kg of body weight per day.

cdc2/cyclin B1 Kinase Assay cdc2/cyclin B1 kinase activity was determined by monitoring the incorporation of $^{32}P$ into histone HI. The reaction consisted of 50 ng baculovirus expressed GST-cdc2, 75 ng baculovirus expressed GST-cyclin B1, 1 $\mu$g histone HI (Boehringer Mannheim), 0.2 $\mu$Ci of $^{32}P$ $\gamma$-ATP and 25 $\mu$uM ATP in kinase buffer (50 mM Tris, pH 8.0, 10 mM $MgCl_2$, 1 mM EGTA, 0.5 mM DTT). The reaction was to incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Marshak, D. R., Vanderberg, M. T., Bae, Y. S., Yu, I. J., *J. of Cellular Biochemistry*, 45, 391–400 (1991), incorporated by reference herein).

cdk2/cyclin E Kinase Assay cdk2/cyclin E kinase activity was determined by monitoring the incorporation of $^{32}P$ into the retinoblastoma protein. The reaction consisted of 2.5 ng baculovirus expressed GST-cdk2/cyclin E, 500 ng bacterially produced GST-retinoblastoma protein (aa 776-928), 0.2 $\mu$Ci $^{32}P$ $\gamma$-ATP and 25 $\mu$M ATP in kinase buffer (50 mM Hepes, pH 8.0, 10 mM $MgCl_2$, 5 mM EGTA, 2 mM DTT). The reaction was incubated at 30° C. for 30 minutes and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter.

cdk 4/cyclin D1 Kinase Activity cdk4/cyclin D1 kinase activity was determined by monitoring the incorporation of $^{32}P$ in to the retinoblastoma protein. The reaction consisted of 165 ng baculovirus expressed as GST-cdk4, 282 ng bacterially expressed as S-tag cyclin D1, 500 ng bacterially produced GST-retinoblastoma protein (aa 776-928), 0.2 $\mu$Ci $^{32}P$ $\gamma$-ATP and 25 $\mu$M ATP in kinase buffer (50 mM Hepes, pH 8.0, 10 mM MgCl$_2$, 5 mM EGTA, 2 mM DTT). The reaction was incubated at 30° C. for 1 hour and then stopped by the addition of cold trichloroacetic acid (TCA) to a final concentration of 15% and incubated on ice for 20 minutes. The reaction was harvested onto GF/C unifilter plates (Packard) using a Packard Filtermate Universal harvester, and the filters were counted on a Packard TopCount 96-well liquid scintillation counter (Coleman, K. G., Wautlet, B. S., Morissey, D, Mulheron, J. G., Sedman, S., Brinkley, P., Price, S., Webster, K. R. (1997) Identification of CDK4 Sequences involved in cyclin D, and p16 binding. *J. Biol. Chem.* 272,30:18869–18874, incorporated by reference herein).

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Preparation of 4-(Aminomethyl)-N-[5-[[[5-(1,1-dimethylethyl)-2-oxazolyl]methyl]thio]-2-thiazolyl]benzeneacetamide

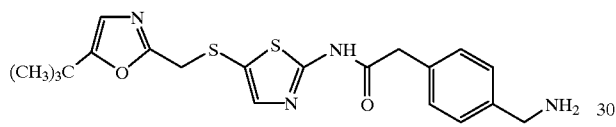

A. 1-Azido-3,3-dimethyl-2-butanone

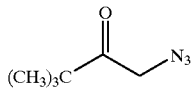

1-Bromo-3,3-dimethyl-2-butanone (199.07 g, 1.115 mol, 1 eq) was combined in 1.785 L of acetone with sodium azide (93.9 g, 1.444 mol, 1.3 eq). The reaction mixture was stirred at rt for 27.5 h. The resulting slurry was filtered and washed with acetone (3×150 mL). The filtrate was concentrated in vacuo to provide 154.3 g (98.4%) of 1-azido-3,3-dimethyl-2-butanone. HPLC 83.85% at 2.57 min (Phenomenex 5 m C18 column 4.6×50 mm, 10–90% aqueous methanol over 4 minutes containing 0.2% phosphoric acid, 4 mL/min, monitoring at 220 nm).

B. 1-Amino-3,3-dimethyl-2-butanone hydrochloride

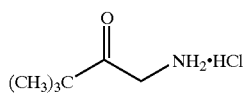

1-Azido-3,3-dimethyl-2-butanone (400 g, 1.254 mol, 1 eq) was combined in 2 L of ethanol with 12 N aqueous HCl (439 mL, 5.26 mol, 4.2 eq). The reaction mixture was stirred at 75° C. for 1 h and then allowed to cool to rt. The resulting slurry was filtered. The filtrate was concentrated in vacuo and isopropyl alcohol was added. The solution was filtered again. Addition of 1.2 L of ether caused the desired material to precipitate from solution. The material was filtered, washed with ether (2×300 mL), and dried in vacuo at 50° C. overnight to provide 184.1 g (97%) of 1-amino-3,3-dimethyl-2-butanone hydrochloride.

C. N-Chloroacetyl-1-amino-3,3-dimethyl-2-butanone

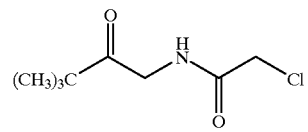

1-Amino-3,3-dimethyl-2-butanone hydrochloride (130.96 g, 0.8637 mol, 1 eq) was dissolved in 3.025 L of CH$_2$Cl$_2$ under N$_2$ at −5° C. Triethylamine (301 mL, 2.16 mol, 2.5 eq) was added followed by chloroacetyl chloride (75.7 mL, 0.450 mol, 1.1 eq) in 175 mL of CH$_2$Cl$_2$. The resulting slurry was stirred at −5 to −10° C. for 2 h. Water (1.575 L) was added followed by 175 mL of concentrated HCl. The organic phase was washed a second time with 1.75 L of 10% aqueous HCR, and then with 500 mL of water. The organic phase was dried over Na$_2$SO$_4$ and concentrated in vacuo to provide 155.26 g (93.8%) of N-chloroacetyl-1-amino-3,3-dimethyl-2-butanone. HPLC R.T.=2.27 min (Phenomenex 5 m C18 column 4.6×50 mm, 10–90% aqueous methanol over 4 minutes containing 0.2% phosphoric acid, 4 mL/min, monitoring at 220 nm).

D. 5-t-Butyl-2-chloromethyloxazole

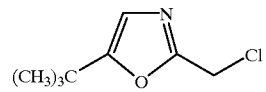

N-Chloroacetyl-1-amino-3,3-dimethyl-2-butanone (180.13 g, 0.9398 mol, 1 eq) was combined with phosphorus oxychloride (262 mL, 2.8109 mol, 3 eq) under N$_2$. The reaction mixture was heated at 105° C. for 1 h. The mixture was cooled to rt and then quenched with 1.3 kg of ice. The aqueous phase was extracted with ethyl acetate (1 L, then 2×500 mL). The organic extracts were washed with saturated aqueous NaHCO$_3$ (4×1 L) which was back-extracted several times with ethyl acetate. The organic phases were combined, washed with saturated aqueous NaHCO$_3$ (500 mL) followed by saturated aqueous NaCl (300 mL), dried over MgSO$_4$, and concentrated in vacuo to give a brown oil. The crude material was distilled under high vacuum at 100° C. to provide 155.92 g (96%) of 5-t-butyl-2-chloromethyloxazole. HPLC R.T.=3.62 min (Phenomenex 5 m C18 column 4.6×50 mm, 10–90% aqueous methanol over 4 minutes containing 0.2% phosphoric acid, 4 mL/min, monitoring at 220 nm).

Alternate method using Burgess' reagent:

As an alternative, 5-t-butyl-2-chloromethyloxazole may be prepared by reaction of a suitable chloroamide with 2 eq of Burgess' salt ((methoxycarbonylsulfamoyl)triethyl ammonium hydroxide inner salt) in tetrahydrofuran.

E. S-[[5-(1,1-Dimethylethyl)-2-oxazolyl]methyl]thiourea

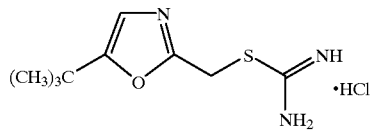

5-t-Butyl-2-chloromethyloxazole (1.77 g, 10.2 mmol, 1.02 eq) was combined with thiourea (0.76 g, 9.98 mmol, 1 eq) under N$_2$ in 10 mL of absolute ethanol. The reaction mixture was heated at reflux for 1.5 h. The mixture was cooled to rt and concentrated in vacuo. Trituration of the resulting crude material with t-butyl methyl ether provided 2.32 g (93%) of S-[[5-(1,1-dimethylethyl)-2-oxazolyl]methyl]thiourea. HPLC R.T.=2.05 min (Phenomenex 5 m C18 column 4.6×50 mm, 10–90% aqueous methanol over 4 minutes containing 0.2% phosphoric acid, 4 mL/min, monitoring at 220 nm); $^1$H NMR (d-DMSO): 9.48 (s, 3H), 6.85 (s, 1H), 4.73 (s, 2H), 1.24 (s, 9H).

F. 2-Amino-5-[[[5-(1,1-dimethylethyl)-2-oxazolyl]methyl]thio]thiazole

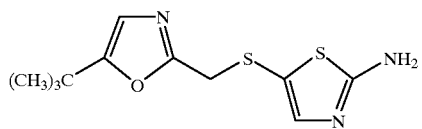

S-[[5-(1,1-Dimethylethyl)-2-oxazolyl]methyl]thiourea (1.25 g, 5 mmol, 1 eq) was added to a mixture of NaOH (3.0 g, 75 mmol, 15 eq), water (10 mL), toluene (10 mL), and tetrabutylammonium sulfate (50 mg, 0.086 mmol, 0.017 eq). 5-Bromo-2-aminothiazole hydrobromide (1.70 g, 5 mmol, 1 eq) was added and the reaction mixture was stirred at rt for 14.5 h, diluted with water and extracted twice with ethyl acetate. The organic extracts were washed with water (4×10 mL), dried over MgSO$_4$, and concentrated in vacuo to provide 1.1 g (82%) of 2-amino-5-[[[5-(1,1-dimethylethyl)-2-oxazolyl]methyl]thio]thiazole. HPLC 86.3% at 2.75 min (Phenomenex 5 m C18 column 4.6×50 mm, 10–90% aqueous methanol over 4 minutes containing 0.2% phosphoric acid, 4 mL/min, monitoring at 220 nm); $^1$H NMR (CDCl$_3$): 6.97 (s, 1H), 6.59 (s, 1H), 5.40 (br s, 2H), 3.89 (s, 2H), 1.27 (s, 9H).

G. 4-(Bromomethyl)-N-[5-[[[5-(1,1-dimethylethyl)-2-oxazolyl]methyl]thio]-2-thiazolyl]benzeneacetamide

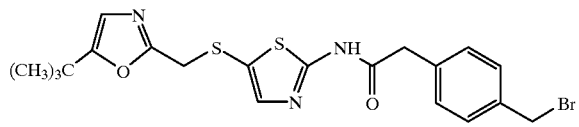

1,3-Dicyclohexylcarbodiimide (7.18 g, 34.8 mmol, 1.25 eq) was added to a mixture of 2-amino-5-[[[5-(1,1-dimethylethyl)-2-oxazolyl]methyl]thio]thiazole (7.5 g, 27.8 mmol, 1 eq), and 4-bromomethylphenylacetic acid (7.97 g, 34.8 mmol, 1.25 eq) in 175 mL of CH$_2$Cl$_2$ at 0° C. The reaction mixture was allowed to warm to rt. After 30 min LC/MS indicated that the reaction was complete. The mixture was filtered and concentrated in vacuo onto 20 g of silica gel. The material was purified by flash chromatography on silica gel eluting with 60% ethyl acetate in hexanes to provide 11.5 g (83%) of 4-(bromomethyl)-N-[5-[[[5-(1,1-dimethylethyl)-2-oxazolyl]methyl]thio]-2-thiazolyl]benzeneacetamide as a yellow solid.

In an alternative method of preparation, 1-(3-dimethylaminopropyl)-3-ethylcarbodiimide hydrochloride (13.8 g, 72 mmol, 2 eq) was added to a mixture of 2-amino-5-[[[5-(1,1-dimethylethyl)-2-oxazolyl]methyl]thio]thiazole (2.0 g, 7.42 mmol, 1 eq) and 4-bromomethyl phenylacetic acid (2.60 g, 11.3 mmol, 1.5 eq) in CH$_2$Cl$_2$ (30 mL) under N$_2$ at rt. After 1 h, the reaction mixture was diluted with 20 mL of ethyl acetate and washed with saturated aqueous NaHCO$_3$ (2×20 mL). The organic phase was then washed with 10% aqueous citric acid, dried over MgSO$_4$, and concentrated in vacuo to provide a yellow solid. This material was triturated with ether to provide 3.01 g (84.4%) of 4-(bromomethyl)-N-[5-[[[5-(1,1-dimethylethyl)-2-oxazolyl]methyl]thio]-2-thiazolyl]benzeneacetamide. HPLC: R.T.=3.69 min (YMC S5 ODS column 4.6×50 mm, 10–90% aqueous methanol over 4 minutes containing 0.2% phosphoric acid, 4 mL/min, monitoring at 220 nm); $^1$H NMR (CDCl$_3$): 7.37–7.24 (m, 5H), 6.54 (s, 1H), 4.47 (s, 2H), 3.93 (s, 2H), 3.79 (s, 2H), 1.27 (s, 9H).

H. 4-(Aminomethyl)-N-[5-[[[5-(1,1-dimethylethyl)-2-oxazolyl]methyl]thio]-2-thiazolyl]benzeneacetamide

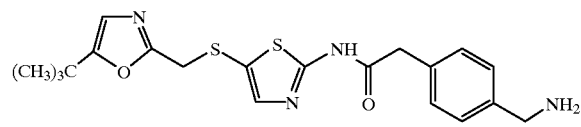

4-(Bromomethyl)-N-[5-[[[5-(1,1-dimethylethyl)-2-oxazolyl]methyl]thio]-2-thiazolyl]benzeneacetamide (70% pure, 1.05 g, 1.53 mmol, 1 eq) was dissolved in 40 mL of N,N-dimethylformamide and cooled to −70° C. Excess liquid ammonia (6 mL) was added, and after sealing the reaction vessel, the mixture was allowed to warm to rt. After 1 h, the reaction was diluted with ethyl acetate, washed with water (20 mL) and saturated aqueous NaCl, dried over MgSO$_4$, and concentrated in vacuo. The resulting yellow oil was purified by preparative HPLC to provide 270 mg (42.4%) of 4-(aminomethyl)-N-[5-[[[5-(1,1-dimethylethyl)-2-oxazolyl]methyl]thio]-2-thiazolyl]benzeneacetamide. MS: 417 [M+H]$^+$; HPLC R.T.=3.17 min (YMC S5 ODS column 4.6×50 mm, 10–90% aqueous methanol over 4 minutes containing 0.2% phosphoric acid, 4 mL/min, monitoring at 220 nm).

EXAMPLE 2

Preparation of N-[5-[[[5-(1,1-Dimethylethyl)-2-oxazolyl]methyl]thio]-2-thiazolyl]-4-[[(3-hydroxy-2,2-dimethylpropyl)amino]methyl]benzeneacetamide

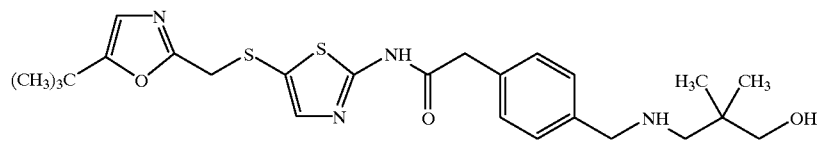

A. 4-Formylphenylacetic acid

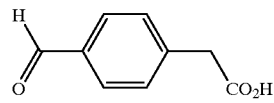

4-Bromophenylacetic acid (10.075 g, 50 mmol, 1 eq) was dissolved in 250 mL of anhydrous terahydrofuran and cooled to −60° C. Phenyllithium (1.8 M in 70% cyclohexane in ether, 65 mL, 117 mmol, 2.34 eq) was added, and the reaction mixture was stirred for 50 min at −75° C. Tert-butyllithium (1.7M, 90 mL, 153 mmol, 3.06 eq) was then added and the reaction mixture was stirred at −75° C. for 40 min before being allowed to warm to −45° C. After 35 min, the reaction mixture was cooled to −65° C. and 10 mL of anhydrous N,N-dimethylformamide was added. After 30 min, ethyl acetate (150 mL) was added and 1N aqueous HCl was added to bring the pH of the solution to 10. The aqueous phase was separated, acidified with 6N aqueous HCl, and extracted twice with ethyl acetate. The organics were combined, washed with water, dried over MgSO$_4$, and concentrated in vacuo. The resulting crude material was triturated with ether and hexanes to give 1.9 g of beige material. An additional 1.2 g of material was obtained from the filtrate by flash chromatography on silica gel eluting with 3:1:1 hexanes:ethyl acetate:ethanol with 1% acetic acid. Additional product (270 mg) was also obtained from the impure fractions after preparative HPLC to provide a total of 3.37 g (41%) of 4-formylphenylacetic acid.

B. N-[5-[[[5-(1,1-Dimethylethyl)-2-oxazolyl]methyl]thio]-2-thiazolyl]-4-formylbenzeneacetamide

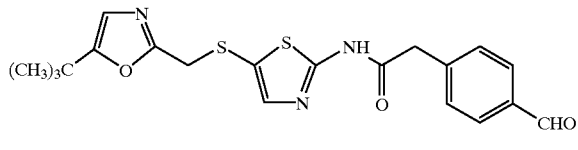

Oxalyl chloride (2.0 M in CH$_2$Cl$_2$, 9.1 mL, 18.2 mmol, 3 eq) was added slowly to a solution of 4-formylphenylacetic acid (2.0 g, 12.2 mmol, 2 eq) in CH$_2$Cl$_2$ at 0° C. The reaction mixture was stirred at 0° C. for 5 min. The resultant acylchloride containing reaction mixture was treated dropwise with a solution of 2-amino-5-[[[5-(1,1-dimethylethyl)-2-oxazolyl]methyl]thio]thiazole (1.64 g, 6.09 mmol) and triethylamine (3.2 mL) in dichloromethane, and allowed to warm to rt over 30 min. The reaction mixture was diluted with saturated aqueous NaHCO$_3$ and CH$_2$Cl$_2$ (220 mL). The organic phase was separated, washed sequentially with saturated aqueous NaHCO$_3$, 0.1 N HCl and saturated NaCl, and dried over MgSO$_4$. Concentration in vacuo gave a brown oil which was triturated with a hexanes/ethyl acetate solution to provide 1.03 g of yellowish solid. An additional 1.02 g of material was obtained from the filtrate by flash chromatography on silica gel eluting with a gradient of 50–60% ethyl acetate in hexanes. A total of 2.05 g (81%) of N-[5-[[[5-(1,1-dimethylethyl-2-oxazolyl]methyl]thio]-2-thiazolyl]-4-formylbenzeneacetamide was obtained. HPLC: 97% at 3.90 min (YMC S5 ODS column 4.6×50 mm, 10–90% aqueous methanol over 4 minutes containing 0.2% phosphoric acid, 4 mL/min, monitoring at 220 nm).

C. N-[5-[[[5-(1,1-Dimethylethyl)-2-oxazolyl]methyl]thio]-2-thiazolyl]-4-[[(3-hydroxy-2,2-dimethylpropyl)amino]methyl]benzeneacetamide

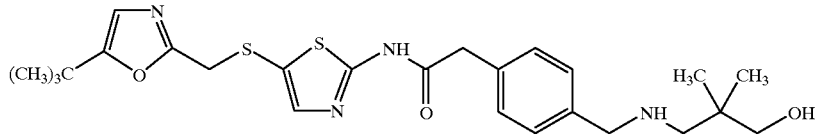

N-[5-[[[5-(1,1-Dimethylethyl)-2-oxazolyl]methyl]thio]-2-thiazolyl]-4-formylbenzeneacetamide (1.1 g, 2.65 mmol, 1 eq) was dissolved in 20 mL of tetrahydrofuran and cooled to 0° C. 3-Amino-2,2-dimethyl-1-propanol (1.0 g, 9.7 mmol, 3.7 eq) was added followed by acetic acid (1 mL) and sodium triacetoxyborohydride (2.6 g, 12.3 mmol, 4.6 eq). The reaction mixture was stirred at rt for 1 h. Aqueous NaHCO$_3$ was added, and the mixture was extracted with ethyl acetate. The organics were combined, washed with water, dried over MgSO$_4$, and concentrated in vacuo. The residue was dissolved in methanol and acidified with 4N HCl in dioxane and purified by flash chromatography on silica gel eluting with 10% methanol in ethyl acetate with 2.7% triethylamine to provide 530 mg (40%) of N-[5-[[[5-(1,1-dimethylethyl)-2-oxazolyl]methyl]thio]-2-thiazolyl]-4-[[(3-hydroxy-2,2-dimethylpropyl)amino]methyl] benzeneacetamide as a beige solid. MS: 503 [M+H]$^+$; HPLC: 97% at 3.28 min (YMC S5 ODS column 4.6×50 mm, 10–90% aqueous methanol over 4 minutes containing 0.2% phosphoric acid, 4 mL/min, monitoring at 220 nm).

EXAMPLE 3

Preparation of N-[5-[[[5-(1,1-Dimethylethyl)-2-oxazolyl]methyl]thio]-2-thiazolyl]-4-(1-pyrrolidinylmethyl)benzeneacetamide hydrochloride

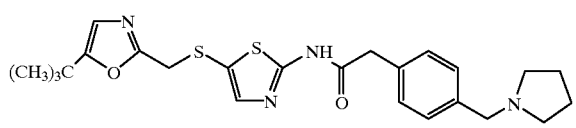

4-(Bromomethyl)-N-[5-[[[5-(1,1-dimethylethyl)-2-oxazolyl]methyl]thio]-2-thiazolyl]benzeneacetamide (2.0 g, 4.2 mmol, 1 eq) was dissolved in 25 mL of N,N-dimethylformamide and added to a solution of pyrrolidine (5.21 mL, 62.4 mmol, 15 eq) in 50 mL of N,N-dimethylformamide at 0° C. The reaction mixture was stirred at 0° C. for 15 min and then allowed to stir at rt overnight. The mixture was diluted with 500 mL of ethyl acetate. The organic phase was washed sequentially with saturated aqueous NaCl and saturated aqueous NaHCO$_3$, dried over MgSO$_4$, and concentrated in vacuo. The crude material was purified by preparative HPLC (C18 50×500 mm column, 50–100% aqueous methanol over 30 minutes) followed by lyophilization (2×1N aqueous HCl, 1×water) to provide 195 mg (10%) of N-[5-[[[5-(1,1-dimethylethyl)-2-oxazolyl]methyl]thio]-2-thiazolyl]-4-(1-pyrrolidinylmethyl) benzeneacetamide hydrochloride as a yellow solid. MS: 471 [M+H]$^+$; HPLC: 97% at 3.17 min (YMC S5 ODS column 4.6×50 mm, 10–90% aqueous methanol over 4 minutes containing 0.2% phosphoric acid, 4 mL/min, monitoring at 220 nm).

EXAMPLE 4

Preparation of N-[5-[[[5-(1,1-Dimethylethyl)-2-oxazolyl]methyl]thio]-2-thiazolyl]-4-[[(2-hydroxyethyl)amino]methyl]benzeneacetamide hydrochloride

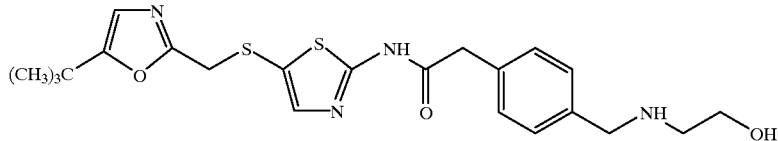

4-(Bromomethyl)-N-[5-[[[5-(1,1-dimethylethyl)-2-oxazolyl]methyl]thio]-2-thiazolyl]benzeneacetamide (10.47 g, 21.8 mmol, 1 eq) was dissolved in 100 mL of N,N-dimethylformamide and added to a solution of ethanolamine (19.73 mL, 0.327 mol, 15 eq) in 200 mL of N,N-dimethylformamide at 0° C. The reaction mixture was stirred at 0° C. for 1 h and diluted with 700 mL of ethyl acetate. The organic extract was washed sequentially with water and saturated aqueous NaHCO$_3$ (4×300 mL), dried over MgSO$_4$, and concentrated in vacuo. The crude material was purified by preparative HPLC (C18 50×500 mm column, 50–100% aqueous methanol over 30 minutes) followed by lyophilization (2×1N aqueous HCl, 1×water) to provide 4.8 g (47.8%) of N-[5-[[[5-(1,1-dimethylethyl)-2-oxazolyl]methyl]thio]-2-thiazolyl]-4-[[(2-hydroxyethyl)amino]methyl]benzeneacetamide hydrochloride as a yellow solid. MS: 461 [M+H]$^+$; HPLC: 97% at 3.15 min (YMC S5 ODS column 4.6×50 mm, 10–90% aqueous methanol over 4 minutes containing 0.2% phosphoric acid, 4 mL/min, monitoring at 220 nm).

EXAMPLE 5

Preparation of N-[5-[[[5-(1,1-Dimethylethyl)-2-oxazolyl]methyl]thio]-2-thiazolyl]-4-[[[2-(1-pyrrolidinyl)ethyl]amino]methyl]benzeneacetamide N-[5-[[[5-(1,1-Dimethylethyl)-2-oxazolyl]methyl]thio]-2-thiazolyl]-4-(formyl)benzeneacetamide (0.70 g, 1.68 mmol, 1 eq) was dissolved in 28 mL of tetrahydrofuran under argon. 1-(2-Aminoethyl)pyrrolidine (1.0 mL, 7.89 mmol, 4.7 eq) was added followed by acetic acid (1 mL) and sodium triacetoxyborohydride (2.07 g, 9.28 mmol, 5.5 eq). The reaction mixture was stirred at rt for 30 min. Aqueous NaHCO$_3$ was added, and the mixture was extracted with ethyl acetate. The organic extracts were dried over MgSO$_4$ and concentrated in vacuo. The material was purified by flash chromatography on silica gel eluting with a gradient of 15–30% methanol in ethyl acetate with 0.6% ammonium hydroxide to provide 602 mg (70%) of N-[5-[[[5-(1,1-dimethylethyl)-2-oxazolyl]methyl]thio]-2-thiazolyl]-4-[[[2-(1-pyrrolidinyl)ethyl]amino]methyl]benzeneacetamide. The dihydrochloride salt may be obtained as a pale fluffy solid by adding 2.34 mL of 1 N aqueous HCl and subsequent lyophilization. MS: 514 [M+H]$^+$; HPLC: 100% at 2.93 min (YMC S5 ODS column 4.6×50 mm, 10–90% aqueous methanol over 4 minutes containing 0.2% phosphoric acid, 4 mL/min, monitoring at 220 nm).

EXAMPLE 6

Preparation of N-[5-[[[5-(1,1-Dimethylethyl)-2-oxazolyl]methyl]thio]-2-thiazolyl]-4-[[(2-hydroxy-1,1-dimethylethyl)amino]methyl]benzeneacetamide hydrochloride

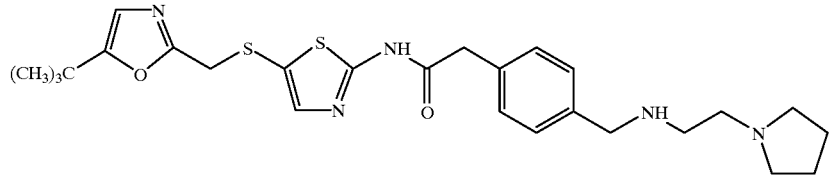

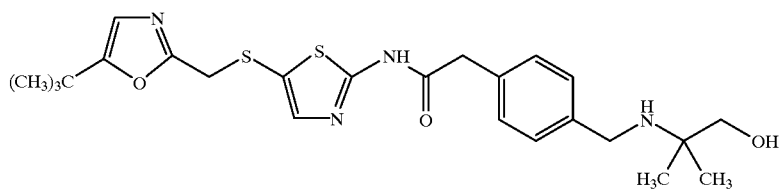

To a solution of 1,1-dimethylethanolamine (1.08 g) in N,N-dimethylformamide (1.25 mL) was added at 0° C. a solution of 4-(bromomethyl)-N-[5-[[[5-(1,1-dimethylethyl)-2-oxazolyl]methyl]thio]-2-thiazolyl]benzeneacetamide (600 mg) in N,N-dimethylformamide (3 mL). The reaction mixture was stirred at room tempaerature for 30 minutes, and purified by preparative HPLC using a methanol:water gradient. The desired fractions were combined, concentrated in vacuo and lyophillized to provide the product as free base. The free base was treated with hydrochloric acid in dioxane (4 N, 0.48 mL) and concentrated in vacuo to provide the hydrochloride salt of N-[5-[[[5-(1,1-dimethylethyl)-2-oxazolyl]methyl]thio]-2-thiazolyl]-4-[[(2-hydroxy-1,1-dimethylethyl)amino]methyl]benzeneacetamide (460 mg). HPLC R.T.=2.66 min (YMC S5 ODS column 4.6×50 mm, 10–90% aqueous methanol over 4 minutes containing 0.2% phosphoric acid, 4 mL/min, monitoring at 220 nm). MS: 489 [M+H]+.

EXAMPLE 7

Preparation of N-[5-[[[5-(1,1-Dimethylethyl)-2-oxazolyl]methyl]thio]-2-thiazolyl]-3-[[(2-hydroxyethyl)amino]methyl]benzeneacetamide hydrochloride was concentrated in vacuo for 1.5 h at rt. The acid chloride intermediate was dissolved in 60 mL of $CH_2Cl_2$ and the resultant solution was added over 40 min to a solution of 2-amino-5-[[[5-(1,1-dimethylethyl)-2-oxazolyl]methyl]thio]thiazole and triethylamine (5.90 mL, 42.3 mmol, 3.15 eq) in 120 mL of $CH_2Cl_2$ at 0° C. The reaction mixture was stirred at 0° C. for 30 min. Saturated aqueous $NaHCO_3$ was added and the mixture was extracted with $CH_2Cl_2$. The organic extract was washed sequentially with 0.05 N aqueous HCl and saturated aqueous NaCl, and dried over $MgSO_4$. The organic phase was concentrated in vacuo to provide a brown oil which was triturated with ether to afford 5.04 g (90.6%) of N-[5-[[[5-(1,1-dimethylethyl)-2-oxazolyl]methyl]thio]-2-thiazolyl]-3-formylbenzeneacetamide. HPLC: 87% at 3.930 min (YMC S5 ODS column 4.6×50 mm, 10–90% aqueous methanol over 4 minutes containing 0.2% phosphoric acid, 4 mL/min, monitoring at 220 nm).

B. N-[5-[[[5-(1,1-Dimethylethyl)-2-oxazolyl]methyl]thio]-2-thiazolyl]-3-[[(2-hydroxyethyl)amino]methyl]benzeneacetamide hydrochloride

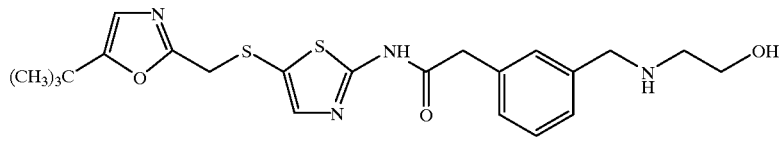

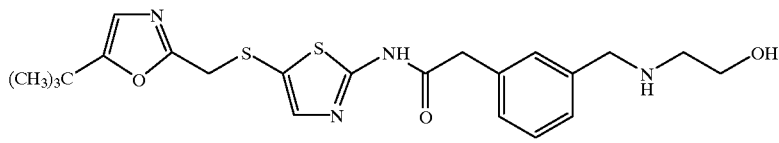

A. N-[5-[[[5-(1,1-Dimethylethyl)-2-oxazolyl]methyl]thio]-2-thiazolyl]-3-formylbenzeneacetamide

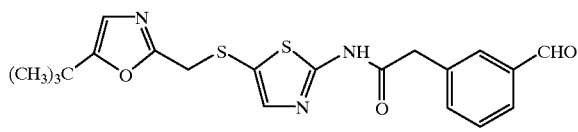

Oxalyl chloride (2.0 M in $CH_2Cl_2$, 21.0 mL, 42.0 mmol, 3.13 eq) was added over 20 min to a solution of 3-(formyl)phenylacetic acid (75%, 3.5 g, 16.0 mmol, 1.2 eq) in $CH_2Cl_2$ with a few drops of N,N-dimethylformamide at 0° C. The reaction mixture was stirred at 0° C. for 20 min and then allowed to warm to rt. After 10 min, the reaction mixture Ethanolamine (0.73 mL, 12.1 mmol, 5 eq) was added to a solution of N-[5-[[[5-(1,1-dimethylethyl)-2-oxazolyl]methyl]thio]-2-thiazolyl]-3-(formyl)benzeneacetamide (1.0 g, 2.4 mmol, 1 eq) in 60 mL of anhydrous tetrahydrofuran under $N_2$. The reaction mixture was stirred for 15 min. Acetic acid (1 mL) and sodium triacetoxyborohydride (2.97 g, 14.0 mmol, 5.8 eq) were added and the reaction mixture was stirred for 40 min. Aqueous $NaHCO_3$ was added, and the mixture was extracted with ethyl acetate (3×80 mL). The organic extracts were dried over $MgSO_4$ and concentrated in vacuo. The material was purified by flash chromatography on silica gel eluting with a gradient of 10–20% methanol in ethyl acetate with 0.2–0.4% ammonium hydroxide. Acidification with 1.5 mL of 1 N aqueous HCl and subsequent lyophilization provided 686 mg (57.5%) of N-[5-[[[5-(1,1-dimethylethyl)-2-oxazolyl]methyl]thio]-2-thiazolyl]-3-[[(2-hydroxyethyl)amino]methyl]benzeneacetamide hydrochlo-

EXAMPLE 8

Preparation of N-[5-[[[5-(1,1-Dimethylethyl)-2-oxazolyl]methyl]thio]-2-thiazolyl]-3-[[(3-hydroxy-2,2-dimethylpropyl)amino]methyl]benzeneacetamide

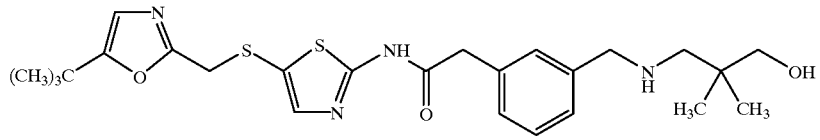

3-Amino-2,2-dimethyl-1-propanol (0.37 g, 3.59 mmol, 5 eq) was added to a solution of N-[5-[[[5-(1,1-dimethylethyl)-2-oxazolyl]methyl]thio]-2-thiazolyl]-3-(formyl)benzeneacetamide (300 mg, 0.72 mmol, 1 eq) in 20 mL of anhydrous tetrahydrofuran under $N_2$. Acetic acid (0.5 mL) and sodium triacetoxyborohydride (0.80 g, 3.58 mmol, 5 eq) were added and the reaction mixture was stirred for 1.5 h. Aqueous $NaHCO_3$ was added, and the mixture was extracted with ethyl acetate. The organic extracts were dried over $MgSO_4$ and concentrated in vacuo. The crude material was purified by flash chromatography on silica gel eluting with a gradient of 10–20% methanol in ethyl acetate with 0.5% ammonium hydroxide to afford 0.206 g (57%) of N-[5-[[[5-(1,1-dimethylethyl)-2-oxazolyl]methyl]thio]-2-thiazolyl]-3-[[(3-hydroxy-2,2-dimethylpropyl)amino]methyl]benzeneacetamide. Acidification with 1 N aqueous HCl and subsequent lyophilization provided the hydrochloride salt as an off-white fluffy solid. MS: 583 [M+H]$^+$; HPLC: R.T.=3.38 min (YMC S5 ODS column 4.6×50 mm, 10–90% aqueous methanol over 4 minutes containing 0.2% phosphoric acid, 4 mL/min, monitoring at 220 nm).

EXAMPLE 9

Preparation of 3-(Aminomethyl)-N-[5-[[[5-(1,1-dimethylethyl)-2-oxazolyl]methyl]thio]-2-thiazolyl]benzeneacetamide

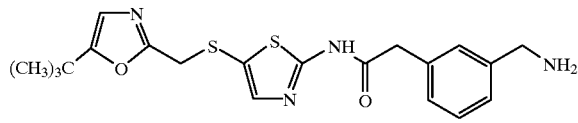

To a solution of N-[5-[[[5-(1,1-dimethylethyl)-2-oxazolyl]methyl]thio]-2-thiazolyl]-3-(formyl)benzeneacetamide (1.51 g, 3.63 mmol) in acetonitrile (20 mL) under nitrogen atmosphere was added t-butyl material (1.26 g, 10.7 mmol), followed by trifluoroacetic acid (0.54 mL) and triethylsilane (1.71 mL, 10.7 mmol). The reaction mixture was stirred at rt for 20 hr and diluted with ether. The resultant organic solution was washed sequentially with saturated sodium bicarbonate solution and saturated sodium chloride solution, dried over sodium sulfate, and evaporated to dryness to give 2.55 grams of crude material. The crude material was dissolved in dichloromethane (35 mL), cooled to 0° C. and trifluoroacetic acid was added (15 mL). The reaction mixture was stirred at room temperature for 16 hr, concentrated in vacuo, and purified by preparative HPLC to give 3-(aminomethyl)-N-[5-[[[5-( 1,1-dimethylethyl)-2-oxazolyl]methyl]thio]-2-thiazolyl]benzeneacetamide (472 mg). MS: 417 [M+H]$^+$; HPLC R.T.=3.24 min (YMC S5 ODS column 4.6×50 mm, 10–90% aqueous methanol over 4 minutes containing 0.2% phosphoric acid, 4 mL/min, monitoring at 220 nm).

EXAMPLE 10

Preparation of 4-[[(2,3-Dihydroxypropyl)amino]methyl]-N-[5-[[[5-(1,1-dimethylethyl)-2-oxazolyl]methyl]thio]-2-thiazolyl]benzeneacetamide hydrochloride

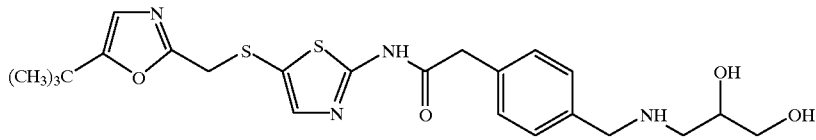

4-(Bromomethyl)-N-[5-[[[5-(1,1-dimethylethyl)-2-oxazolyl]methyl]thio]-2-thiazolyl]benzeneacetamide (2.0 g, 4.16 mmol, 1 eq) was added to 3-amino-1,2-propanediol (5.0 mL, 64.5 mmol, 15.5 eq) in a mixture of 20 mL of N,N-dimethylformamide and 40 mL of anhydrous tetrahydrofuran at rt. The reaction mixture was stirred for 5 h and concentrated in vacuo. The mixture was diluted with 160 mL of ethyl acetate and washed twice with 10% aqueous LiCl and once with saturated aqueous NaCl. The organic phase was dried over $MgSO_4$ and purified by flash chromatography on silica gel eluting with 15% methanol in ethyl acetate with 0.8% ammonium hydroxide to afford 1.08 g (49.3%) of 4-[[(2,3-dihydroxypropyl)amino]methyl]-N-[5-[[[5-(1,1-dimethylethyl)-2-oxazolyl]methyl]thio]-2-thiazolyl]benzeneacetamide. Acidification with 1 N aqueous HCl and subsequent lyophilization provided the hydrochloride salt as a beige solid. MS: 491 [M+H]$^+$; HPLC: R.T.=2.53 min (YMC S5 ODS column 4.6×50 mm, 10–90% aqueous methanol over 4 minutes containing 0.2% phosphoric acid, 4 mL/min, monitoring at 220 nm).

EXAMPLE 11

Preparation of N-[5-[[[5-(1,1-Dimethylethyl)-2-oxazolyl]methyl]thio]-2-thiazolyl]-4-[[[2-hydroxy-1-(hydroxymethyl)ethyl]amino]methyl]benzeneacetamide hydrochloride

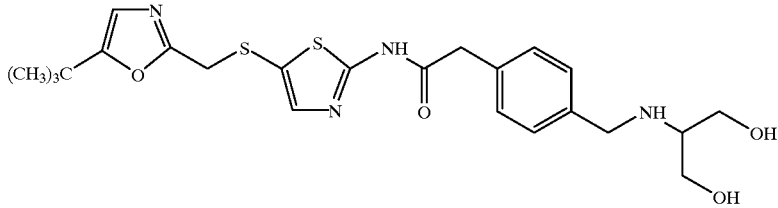

4-(Bromomethyl)-N-[5-[[[5-(1,1-dimethylethyl)-2-oxazolyl]methyl]thio]-2-thiazolyl]benzeneacetamide (1.0 g, 2.08 mmol, 1 eq) was dissolved in 20 mL of N,N-dimethylformamide and added to 2-amino-1,3-propanediol (2.84 g, 31.2 mmol, 15 eq) in 50 mL of N,N-dimethylformamide at 0° C. The reaction mixture was stirred for 18 h at rt. The mixture was diluted with 500 mL of ethyl acetate and washed with saturated aqueous NaCl (2×250 mL) and saturated aqueous NaHCO₃ (3×300 mL). The organic phase was dried over MgSO₄ and concentrated in vacuo. Acidification with 1 N aqueous HCl and subsequent lyophilization provided 790 mg (77.4%) of N-[5-[[[5-(1,1-dimethylethyl)-2-oxazolyl]methyl]thio]-2-thiazolyl]-4-[[[2-hydroxy-1-(hydroxymethyl)ethyl]amino]methyl]benzeneacetamide hydrochloride as a yellow solid. MS: 491 [M+H]⁺; HPLC: R.T.=2.53 min (YMC S5 ODS column 4.6×50 mm, 10–90% aqueous methanol over 4 minutes containing 0.2% phosphoric acid, 4 mL/min, monitoring at 220 nm).

EXAMPLE 12

Preparation of N-[5-[[[5-(1,1-Dimethylethyl)-2-oxazolyl]methyl]thio]-2-thiazolyl]-4-[[(2-hydroxy-1-methylethyl)amino]methyl]benzeneacetamide hydrochloride

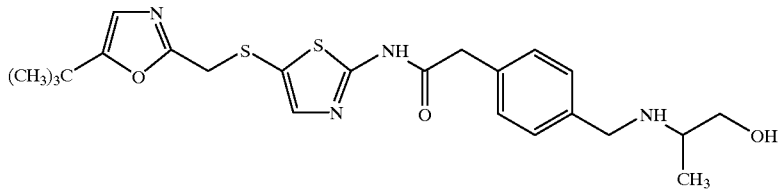

2-Amino-1-propanol (1.88 g, 24.97 mmol, 15 eq) was cooled to 0° C. and 4-(bromomethyl)-N-[5-[[[5-(1,1-dimethylethyl)-2-oxazolyl]methyl]thio]-2-thiazolyl]benzeneacetarnide (0.80 g, 1.66 mmol, 1 eq) was added in 3.75 mL of N,N-dimethylformamide over 5 min. The reaction mixture was stirred for 1 h at rt. The mixture was purified directly by preparative HPLC (Sep Tek column 50×500 mm, 10–100% aqueous methanol over 60 minutes, 45 mL/min, monitoring at 220 nm). Lyophilization of the appropriate fractions gave 658 mg (83.7%) of N-[5-[[[5-(1,1-dimethylethyl)-2-oxazolyl]methyl]thio]-2-thiazolyl]-4-[[(2-hydroxy-1-methylethyl)amino]methyl]benzeneacetamide. Acidification with 4 N HCl in dioxane gave the hydrochloride salt as an off-white solid. MS: 475 [M+H]⁺; HPLC: 100% at 2.60 min (YMC S5 ODS column 4.6×50 mm, 10–90% aqueous methanol over 4 minutes containing 0.2% phosphoric acid, 4 mL/min, monitoring at 220 nm).

EXAMPLE 13

Preparation of N-[5-[[[5-(1,1-Dimethylethyl)-2-oxazolyl]methyl]thio]-2-thiazolyl]-4-[1-[(2-hydroxyethyl)amino]ethyl]benzeneacetamide hydrochloride

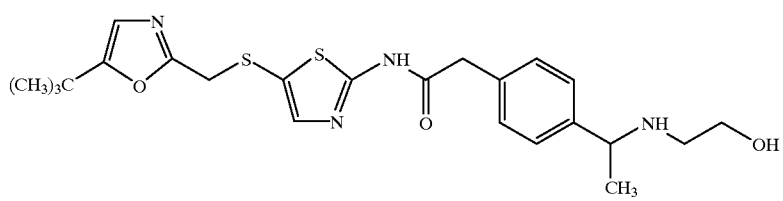

A. 4-(2-(Ethoxycarbonyl)vinyl)phenylacetic acid

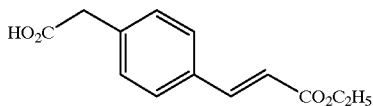

4-Bromophenylacetic acid (86.02 g, 0.748 mol, 1 eq) was dissolved in anhydrous N,N-dimethylformamide under argon at 0° C. with ethyl acrylate (64 mL, 0.591 mol, 0.79 eq), t-butyl acrylate (20 mL, 0.136 mol, 0.18 eq), palladium (II) acetate (1.81 g, 8.06 mmol, 0.01 eq), and triphenylphosphine (4.40 g, 16.7 mmol, 0.022 eq). N,N-diisopropylethylamine (178 mL) was added over 40 min and the reaction mixture was heated at 100° C. for 17 h. The mixture was cooled to rt and diluted with 1.5 L of 1N aqueous HCl. The aqueous phase was extracted with ethyl acetate (3×1L). The organic extracts were washed sequentially with 1N aqueous HCl (2×1L), water (1L) and saturated aqueous NaCl (0.5 L), dried over $Na_2SO_4$, and concentrated in vacuo to give a quantitative yield (107.4 g) of 4-(2-(ethoxycarbonyl)vinyl)phenylacetic acid as a mixture of cis and trans olefins with t-butyl ester.

B. 4-Formylphenylacetic acid

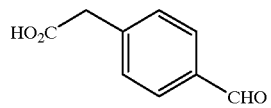

The crude material of Part A (107.4 g) was dissolved in a mixture of 1L of dioxane with 1L of water under Ar. Aqueous osmium tetroxide (10%, 2.0 g) was added followed by sodium periodate (209 g, 0.98 mol) and 4-methylmorpholine N-oxide (2.30 g, 19.6 mmol). After 48 h, the reaction mixture was sparged with argon for 30 min and then stirred for an additional 47 h at rt. The mixture was filtered to remove solid, rinsing with 1 L of ethyl acetate. The aqueous phase was extracted with 1L of ethyl acetate. The combined organic extracts were washed with 1L of water, followed by 0.5 L of 1N aqueous NaOH. The aqueous phase was acidified with 60 mL of concentrated HCl and extracted with 1 L of ethyl acetate. This organic extract was washed with 0.5 L of water, 0.5 L of saturated aqueous NaCl, dried with $MgSO_4$, and concentrated in vacuo to give 36 g of 4-formylphenylacetic acid as a yellow solid.

C. N-[5-[[[5-(1,1-Dimethylethyl)-2-oxazolyl]methyl]thio]-2-thiazolyl]-4-formylbenzeneacetamide

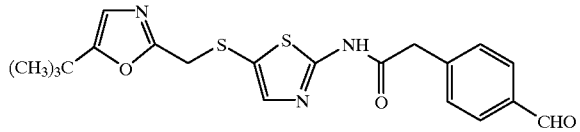

4-Formylphenylacetic acid (1.72 g, 10.5 mmol, 1.1 eq) was combined with 2-amino-5-[[[5-(1,1-dimethylethyl-2-oxazolyl]methyl]thio]thiazole (2.56 g, 9.53 mmol, 1 eq), $CH_2Cl_2$ (20 mL) and 1-(3-dimethylaminopropyl)-3-ethylcarbodiimide hydrochloride (2.61 g, 13.6 mmol, 1.3 eq). The reaction mixture was stirred at rt for 1 h, diluted with 40 mL of $CH_2Cl_2$, and washed sequentially with 1N aqueous HCl (2×20 mL), saturated aqueous $NaHCO_3$ (20 mL) and saturated aqueous NaCl (2×50 mL), dried over $MgSO_4$, and concentrated in vacuo to provide 3.41 g (86%) of N-[5-[[[5-(1,1-dimethylethyl)-2-oxazolyl]methyl]thio]-2-thiazolyl]-4-formylbenzeneacetamide.

D. N-[5-[[[5-(1,1-Dimethylethyl)-2-oxazolyl]methyl]thio]-2-thiazolyl]-4-[(1-hydroxy)ethyl]benzeneacetamide

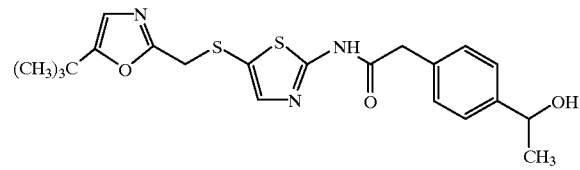

N-[5-[[[5-(1,1-Dimethylethyl)-2-oxazolyl]methyl]thio]-2-thiazolyl]-4-formylbenzeneacetamide (3.315 g, 7.98 mmol, 1 eq) was dissolved in 100 mL of anhydrous tetrahydrofuran under argon at −78° C. Methylmagnesium bromide (3M in ether, 5.60 mL, 16.8 mmol, 2.1 eq) was added over 5 min and the reaction mixture was stirred at −78° C. for 1.75 h. The reaction mixture was quenched with saturated aqueous $NH_4Cl$ and diluted with 100 mL of saturated aqueous $NaHCO_3$. The mixture was extracted with 250 mL of ethyl acetate. The aqueous phase was acidified with 1N aqueous HCl to pH 5 and then extracted with ethyl acetate (2×300 mL). The combined organic extracts were washed with saturated aqueous NaCl (100 mL), dried over $MgSO_4$, and concentrated in vacuo to provide 2.87 g (83%) of N-[5-[[[5-(1,1-dimethylethyl)-2-oxazolyl]methyl]thio]-2-thiazolyl]-4-[(1-hydroxy)ethyl]benzeneacetamide.

E. N-[5-[[[5-(1,1-Dimethylethyl)-2-oxazolyl]methyl]thio]-2-thiazolyl]-4-[(1-chloro)ethyl]benzeneacetamide

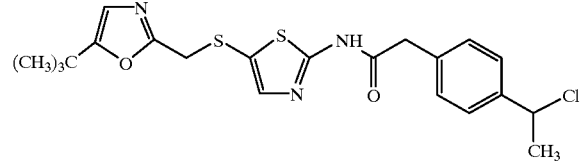

N-[5-[[[5-(1,1-Dimethylethyl)-2-oxazolyl]methyl]thio]-2-thiazolyl]-4-[(1-hydroxy)ethyl]benzeneacetamide (0.550 g, 1.27 mmol, 1 eq) was dissolved in 5.5 mL of anhydrous tetrahydrofuran under argon at 0° C. Thionyl chloride (0.102 mL, 1.40 mmol, 1.1 eq) was added over 6 min and the reaction mixture was stirred at 0° C. for 25 min. The mixture was diluted with 300 mL of ethyl acetate and washed with saturated aqueous $NaHCO_3$ (2×30 mL) and saturated aqueous NaCl (30 mL). The organic phase was dried over $MgSO_4$ and concentrated in vacuo to provide 533 mg (93%) of N-[5-[[[5-(1,1-dimethylethyl)-2-oxazolyl]methyl]thio]-2-thiazolyl]-4-[(1-chloro)ethyl]benzeneacetamide.

F. N-[5-[[[5-(1,1-Dimethylethyl)-2-oxazolyl]methyl]thio]-2-thiazolyl]-4-[1-[(2-hydroxyethyl)amino]ethyl]benzeneacetamide hydrochloride

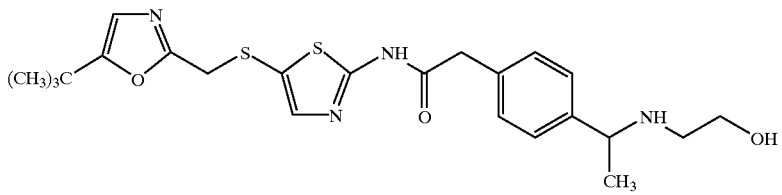

N-[5-[[[5-(1,1-Dimethylethyl)-2-oxazolyl]methyl]thio]-2-thiazolyl]-4-[(1-chloro)ethyl]benzeneacetamide (480 mg, 1.07 mmol, 1 eq) was dissolved in 2.5 mL of N,N-dimethylformamide and added over 7 min to 2-aminoethanol (979 mg, 16.0 mmol, 15 eq) at 0° C. The reaction mixture was stirred at rt for 20 min. The mixture was purified directly by preparative HPLC (Sep Tek column 50×500 mm, 15–100% aqueous methanol over 50 minutes, 45 mL/min, monitoring at 220 nm). The desired fractions were concentrated in vacuo and acidified with 1 N aqueous HCl. Lyophilization gave 220 mg (38%) of N-[5-[[[5-(1,1-dimethylethyl)-2-oxazolyl]methyl]thio]-2-thiazolyl]-4-[1-[(2-hydroxyethyl)amino]ethyl]benzeneacetamide hydrochloride as an off-white solid. MS: 475 [M+H]+; HPLC: 98% at 2.66 min (YMC S5 ODS column 4.6×50 mm, 10–90% aqueous methanol over 4 minutes containing 0.2% phosphoric acid, 4 mL/min, monitoring at 220 nm).

EXAMPLE 14

Preparation of N-[5-[[[5-(1,1-Dimethylethyl)-2-oxazolyl]methyl]thio]-2-thiazolyl]-4-[1-[(2-hydroxy-1-methylethyl)amino]ethyl]benzeneacetamide hydrochloride

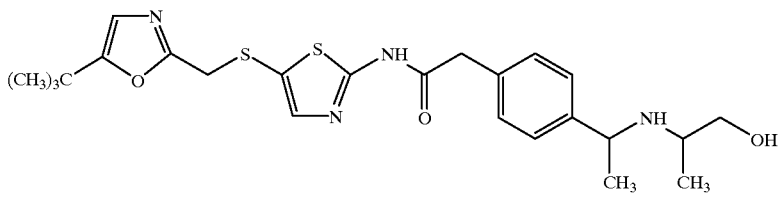

N-[5-[[[5-(1,1-Dimethylethyl)-2-oxazolyl]methyl]thio]-2-thiazolyl]-4-[(1-chloro)ethyl]benzeneacetamide (0.60 g, 1.33 mmol, 1 eq) was dissolved in 3.75 mL of N,N-dimethylformamide and added slowly to 2-amino-1-propanol (1.50 g, 20.0 mmol, 15 eq) at 0° C. The reaction mixture was stirred at rt for 20 min, filtered, and the resulting solid was purified by preparative HPLC (Sep Tek column 50×500 mm, 20–100% aqueous methanol over 50 minutes, 49 mL/min, monitoring at 220 nm). The desired fractions were concentrated in vacuo and acidified with 1 N aqueous HCl. Lyophilization gave 550 mg (79%) of N-[5-[[[5-(1,1-dimethylethyl)-2-oxazolyl]methyl]thio]-2-thiazolyl]-4-[1-[(2-hydroxy-1-methylethyl)amino]ethyl]benzeneacetamide hydrochloride as a white solid. MS: 489 [M+H]+; HPLC: 98% at 2.70 min (YMC S5 ODS column 4.6×50 mm, 10–90% aqueous methanol over 4 minutes containing 0.2% phosphoric acid, 4 mL/min, monitoring at 220 nm).

EXAMPLE 15

Preparation of (S)-N-[5-[[[5-(1,1-Dimethylethyl)-2-oxazolyl]methyl]thio]-2-thiazolyl]-4-[[(2-hydroxyethyl)amino]methyl]-α-methylbenzeneacetamide

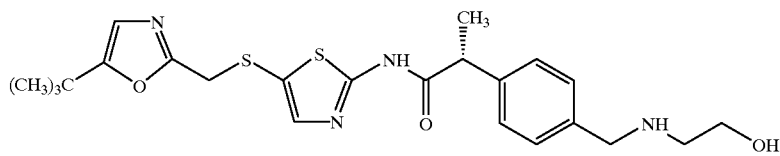

A. (S)-2-[4-Chloromethyl]phenylpropionic acid

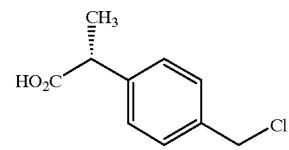

(S)-2-phenylpropionic acid (1.380 g, 9.19 mmol, 1 eq) was combined under argon with 7.0 mL of 37% aqueous HCl, KCl (3.426 g, 45.95 mmol, 5 eq), tetramethylammonium chloride (252 mg, 2.30 mmol, 0.25 eq), and paraformaldehyde (827 mg, 27.6 mmol, 3 eq). The reaction mixture was heated at 100° C. for 22 h, cooled, and extracted with ethyl acetate (2×75 mL). The organic extracts were dried over Na$_2$SO$_4$ and concentrated in vacuo. The material was purified by preparative HPLC to provide 540 mg (54% based on 629 mg of recovered starting material) of (S)-2-[4-chloromethyl]phenylpropionic acid (94% para) as a clear oil. e.e=89%.

B. (S)-4-(Chloromethyl)-N-[5-[[[5-(1,1-dimethylethyl)-2-oxazolyl]methyl]thio]-2-thiazolyl]-α-methylbenzeneacetamide

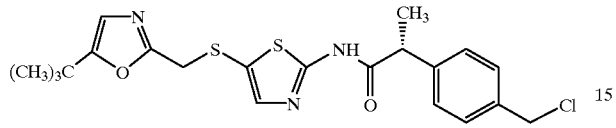

1,3-Dicyclohexylcarbodiimide (617 mg, 2.99 mmol, 1.1 eq) was added to a mixture of 2-amino-5-[[[5-(1,1-dimethylethyl)-2-oxazolyl]methyl]thio]thiazole (732 mg, 2.72 mmol, 1 eq), and (S)-2-[4-chloromethyl] phenylpropionic acid (540 mg, 2.72 mmol, 1 eq) in 10 mL of $CH_2Cl_2$ at rt under argon. After 1.5 h, the mixture was filtered through diatomaceous earth, concentrated in vacuo, and purified by flash chromatography on silica gel eluting with 60% ethyl acetate in hexanes to provide 872 mg (71%) of (S)-4-(chloromethyl)-N-[5-[[[5-(1,1-dimethylethyl)-2-oxazolyl]methyl]thio]-2-thiazolyl]-α-methylbenzeneacetamide as a foamy white solid.

C. (S)-N-[5-[[[5-(1,1-Dimethylethyl)-2-oxazolyl]methyl]thio]-2-thiazolyl]-4-[[(2-hydroxyethyl)amino]methyl]-α-methylbenzeneacetamide

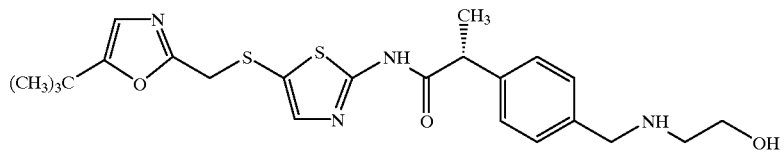

(S)-4-(Chloromethyl)-N-[5-[[[5-(1,1-dimethylethyl)-2-oxazolyl]methyl]thio]-2-thiazolyl]-α-methylbenzeneacetamide (872 mg, 1.94 mmol, 1 eq) was dissolved in 10 mL of N,N-dimethylformamide under argon. 2-Aminoethanol (1.77 g, 29 mmol, 15 eq) was added, and the reaction mixture was stirred at rt for 2 h. The mixture was concentrated in vacuo and purified by preparative HPLC. The desired fractions were concentrated in vacuo to give 610 mg (53%) of (S)-N-[5-[[[5-(1,1-dimethylethyl)-2-oxazolyl]methyl]thio]-2-thiazolyl]-4-[[(2-hydroxyethyl)amino]methyl]-α-methylbenzeneacetamide. Acidification with 1 N aqueous HCl and lyophilization gave the hydrochloride salt as a light yellow solid. MS: 475 [M+H]⁺; HPLC: R.T.=3.23 min (YMC S5 ODS column 4.6×50 mm, 10–90% aqueous methanol over 4 minutes containing 0.2% phosphoric acid, 4 mL/min, monitoring at 220 nm).

EXAMPLE 16

Preparation of N-[5-[[[5-(1,1-Dimethylethyl)-2-oxazolyl]methyl]thio]-2-thiazolyl]-6-[[(2-hydroxyethyl)amino]methyl]-3-pyridineacetamide

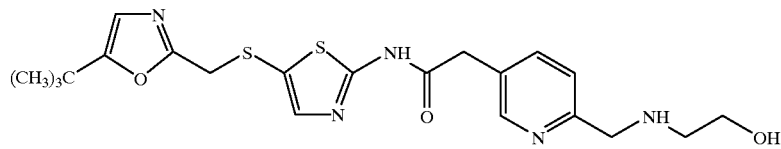

A. Ethyl 6-methyl-3-pyridineacetate, N-oxide

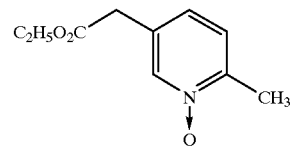

Ethyl 6-methyl-pyridineacetate (1.20 g, 6.70 mmol, 1 eq) was combined with 3-chloroperoxybenzoic acid (50%, 2.77 g, 8.03 mmol, 1.2 eq) in 25 mL of $CHCl_3$. The reaction mixture was stirred at rt for 4 h. The mixture was filtered twice through a 2 inch pad of $Al_2O_3$ eluting with 100 mL of 10% methanol in $CH_2Cl_2$. Concentration in vacuo provided 1.29 g (99%) of ethyl 6-methyl-3-pyridineacetate, N-oxide.

B. Ethyl 6-hydroxymethyl-3-pyridineacetate

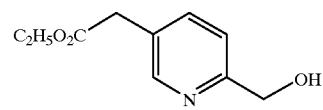

Ethyl 6-methyl-3-pyridineacetate, N-oxide (920 mg, 4.71 mmol, 1 eq) was dissolved in 70 mL of CH$_2$Cl$_2$ and combined with 2,6-lutidine (5.1 mL, 37.7 mmol, 8 eq), and trifluoroacetic anhydride (4.8 mL, 33 mmol, 7 eq). The reaction mixture was heated at 70° C. for 20 min, cooled to rt, and concentrated in vacuo. Absolute ethanol (70 mL) was added followed by concentrated ammonium hydroxide (8.4 mL). The mixture was heated at 45° C. for 20 min, cooled to rt, concentrated in vacuo, and diluted with 120 mL of saturated aqueous NaHCO$_3$. The aqueous phase was extracted with ethyl acetate (3×150 mL). The organic extracts were washed with saturated aqueous NaCl (100 mL), dried with MgSO$_4$, and concentrated in vacuo. Purification by flash chromatography on silica gel eluting with a gradient of 1–2% methanol in CH$_2$Cl$_2$ gave 611 mg (66%) of ethyl 6-hydroxymethyl-3-pyridineacetate.

C. Ethyl 6-[[t-butyldiphenylsilyl]oxy]methyl-3-pyridineacetate

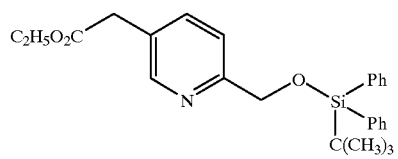

Ethyl 6-hydroxymethyl-3-pyridineacetate (500 mg, 2.56 mmol, 1 eq) was dissolved in 20 mL of CH$_2$Cl$_2$ and combined with triethylamine (0.54 mL, 3.84 mmol, 1.5 eq) and t-butylchlorodiphenylsilane (0.73 mL, 2.82 mmol, 1.1 eq). The reaction mixture was stirred at rt for 4.5 h. An additional 0.25 mL of t-butylchlorodiphenylsilane was added with N,N-dimethylaminopyridine (31 mg, 0.26 nmuol, 0.1 eq). After 2 h, the reaction mixture was diluted with 250 mL of ethyl acetate. The organic phase was washed sequentially with saturated aqueous NaHCO$_3$ (2×40 mL) and saturated aqueous NaCl (100 mL), dried over MgSO$_4$, and concentrated in vacuo. Purification by flash chromatography on silica gel eluting with a gradient of 10–25% ethyl acetate in hexanes gave 795 mg (72%) of ethyl 6-[[t-butyldiphenylsilyl]oxy]methyl-3-pyridineacetate.

D. 6-[[t-Butyldiphenylsilyl]oxy]methyl-3-pyridineacetic acid

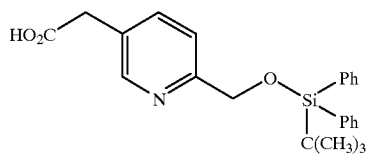

Ethyl 6-[[t-butyldiphenylsilyl]oxy]methyl-3-pyridineacetate (786 mg, 1.81 mmol, 1 eq) was dissolved in 8 mL of methanol and combined with 1 N aqueous NaOH (3 mL, 3 mmol, 1.65 eq). The reaction mixture was stirred at rt for 1 h, diluted with 50 mL of 5% aqueous citric acid, and extracted with ethyl acetate (3×70 mL). The organic phase was washed sequentially with water (40 mL) and saturated aqueous NaCl (100 mL), dried over MgSO$_4$, and concentrated in vacuo to provide 691.7 mg (94%) of 6-[[t-butyldiphenylsilyl]oxy]methyl-3-pyridineacetic acid.

E. N-[5-[[[5-(1,1-Dimethylethyl)-2-oxazolyl]methyl]thio]-2-thiazolyl]-6-[[t-butyldiphenylsilyl]oxy]methyl-3-pyridineacetamide

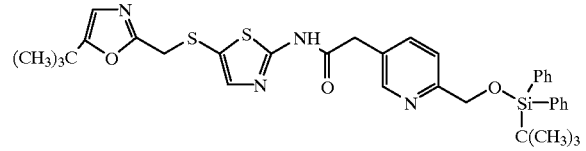

6-[[t-Butyldiphenylsilyl]oxy]methyl-3-pyridineacetic acid (681 mg, 1.68 mmol, 1 eq) was combined with 2-amino-5-[[[5-(1,1-dimethylethyl)-2-oxazolyl]methyl]thio]thiazole (453 mg, 1.68 mmol, 1 eq), CH$_2$Cl$_2$ (5 mL), 2,6-lutidine (0.5 mL) and 1-(3-dimethylaminopropyl)-3-ethylcarbodiimide hydrochloride (354.4 mg, 1.84 mmol, 1.1 eq). The reaction mixture was stirred at rt for 1.5 h, diluted with 250 mL of ethyl acetate, and washed sequentially with 5% aqueous citric acid (2×60 mL), saturated aqueous NaHCO$_3$ (50 mL) and saturated aqueous NaCl (50 mL). The organic phase was dried over MgSO$_4$, concentrated in vacuo, and purified by flash chromatography on silica gel eluting with a gradient of 1–9% methanol in CH$_2$Cl$_2$ to provide N-[5-[[[5-(1,1-dimethylethyl)-2-oxazolyl]methyl]thio]-2-thiazolyl]-6-[[t-butyldiphenylsilyl]oxy]methyl-3-pyridineacetamide (774 mg, 70%).

F. N-[5-[[[5-(1,1-Dimethylethyl)-2-oxazolyl]methyl]thio]-2-thiazolyl]-6-hydroxymethyl-3-pyridineacetamide

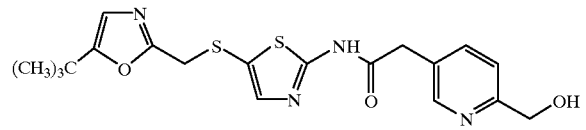

The product of Example 16, Part E (760 mg, 1.16 mmol, 1 eq) was dissolved in 15 mL of anhydrous tetrahydrofuran and combined with tetrabutylammonium fluoride (1.0 M in tetrahydrofuran, 3 mL, 3.0 mmol, 2.6 eq). The reaction mixture was stirred at rt for 1 h, diluted with 100 mL of 5% aqueous citric acid, and extracted with ethyl acetate (3×120 mL). The organic extracts were washed sequentially with saturated aqueous NaHCO$_3$ (60 mL) and saturated aqueous NaCl (60 mL), dried over MgSO$_4$, and concentrated in vacuo. Purification by flash chromatography on silica gel eluting with 6% methanol in CH$_2$Cl$_2$ provided N-[5-[[[5-(1,1-dimethylethyl)-2-oxazolyl]methyl]thio]-2-thiazolyl]-6-hydroxymethyl-3-pyridineacetamide (411 mg, 85%) as a colorless solid. HPLC: 100% at 2.50 min (YMC S5 ODS column 4.6×50 mm, 10–90% aqueous methanol over 4 minutes containing 0.2% phosphoric acid, 4 mL/min, monitoring at 220 nm).

G. N-[5-[[[5-(1,1-Dimethylethyl)-2-oxazolyl]methyl]thio]-2-thiazolyl]-6-chloromethyl-3-pyridineacetamide

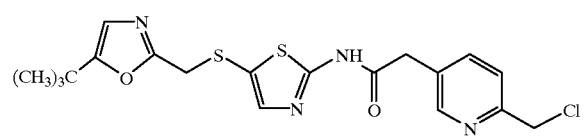

To a solution of N-[5-[[[5-(1,1-dimethylethyl)-2-oxazolyl]methyl]thio]-2-thiazolyl]-6-hydroxymethyl-3-pyridineacetamide (410 mg) in chloroform (10 mL) was added thionyl chloride (79 uL, 1.8 mmol) at rt. The reaction mixture was stirred for 30 min, diluted with saturated sodium bicarbonate solution, and extracted with ethyl acetate (3×120 mL). The combined organic extracts were washed with saturated sodium chloride solution (2×30 mL), dried over magnesium sulfate, filtered and concentrated in vacuo to give the crude product (480 mg), which was purified by chromatography to give N-[5-[[[5-(1,1-dimethylethyl)-2-oxazolyl]methyl]thio]-2-thiazolyl]-6-chloromethyl-3-pyridineacetamide (328 mg, 77%).

H. N-[5-[[[5-(1,1-Dimethylethyl)-2-oxazolyl]methyl]thio]-2-thiazolyl]-6-[[(2-hydroxyethyl)amino]methyl]-3-pyridineacetamide

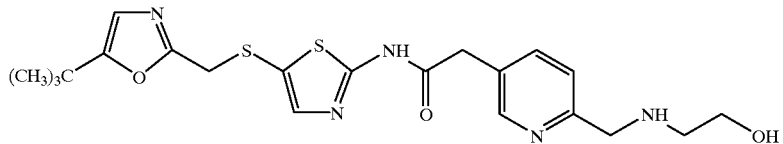

To aminoethanol (681 mg) was added a solution of N-[5-[[[5-(1,1-dimethylethyl)-2-oxazolyl]methyl]thio]-2-thiazolyl]-6-chloromethyl-3-pyridineacetamide (325 mg, 0.74 mmol) in N,N-dimethylformamide (1 mL). The reaction mixture was stirred for 1 hr at rt, diluted with methanol and filtered to give the crude product. N-[5-[[[5-(1,1-Dimethylethyl)-2-oxazolyl]methyl]thio]-2-thiazolyl]-6-[[(2-hydroxyethyl)amino]methyl]-3-pyridineacetamide was obtained after purification by preparative HPLC (248 mg, 72%).

EXAMPLE 17
Preparation of (R)-4-[[(2,3-Dihydroxypropyl)amino]methyl]-N-[5-[[[5-(1,1-dimethylethyl)-2-oxazolyl]methyl]thio]-2-thiazolyl]benzeneacetamide hydrochloride

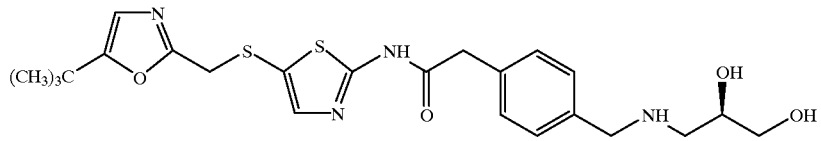

(R)-3-Amino-1,2-propanediol (5.0 g, 54.9 mmol, 10.5 eq) was dissolved in 50 mL of N,N-dimethylformamide under $N_2$. 4-(Bromomethyl)-N-[5-[[[5-(1,1-dimethylethyl)-2-oxazolyl]methyl]thio]-2-thiazolyl]benzeneacetamide (2.50 g, 5.20 mmol, 1 eq) was added in small portions and the reaction mixture was stirred for 2 h at rt. The mixture was diluted with ethyl acetate (250 mL) and washed with water and 10% aqueous LiCl. The aqueous phase was back-extracted twice with ethyl acetate. The organic extracts were dried over $MgSO_4$ and concentrated in vacuo. Purification by flash chromatography on silica gel eluting with a gradient of 10–20% methanol in ethyl acetate with 0.5% ammonium hydroxide provided 1.80 g (65.6%) of (R)-4-[[(2,3-dihydroxypropyl)amino]methyl]-N-[5-[[[5-(1,1-dimethylethyl)-2-oxazolyl]methyl]thio]-2-thiazolyl]benzeneacetamide. Acidification with 1 N aqueous HCl gave the hydrochloride salt as a white fluffy solid. MS: 491 [M+H]$^+$; HPLC: 98% at 2.54 min (YMC S5 ODS column 4.6×50 mm, 10–90% aqueous methanol over 4 minutes containing 0.2% phosphoric acid, 4 mL/min, monitoring at 220 nm); $[\alpha]_D^{23}$=+0.074° (c 1.0, methanol).

EXAMPLE 18
Preparation of (S)-4-[[(2,3-Dihydroxypropyl)amino]methyl]-N-[5-[[[5-(1,1-dimethylethyl)-2-oxazolyl]methyl]thio]-2-thiazolyl]benzeneacetamide hydrochloride

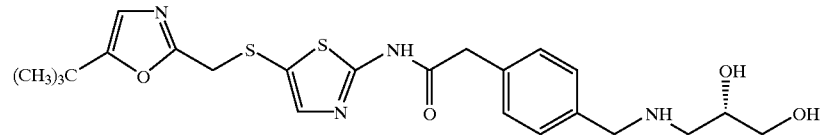

(S)-3-Amino-1,2-propanediol (6.3 g, 68.9 mmol, 13.2 eq) was dissolved in 40 mL of N,N-dimethylformamide under $N_2$. 4-(Bromomethyl)-N-[5-[[[5-(1,1-dimethylethyl)-2-oxazolyl]methyl]thio]-2-thiazolyl]benzeneacetamide (2.50 g, 5.20 mmol, 1 eq) was added in small portions and the reaction mixture was stirred for 1 h at rt. The mixture was diluted with ethyl acetate (300 mL) and washed with ice water and 10% aqueous LiCl. The organic extracts were dried over $MgSO_4$ and concentrated in vacuo. Purification by flash chromatography on silica gel eluting with a gradient of 10–20% methanol in ethyl acetate with 0.6% ammonium hydroxide provided 1.765 g (69%) of (S)-4-[[(2,3-dihydroxypropyl)amino]methyl]-N-[5-[[[5-(1,1-dimethylethyl)-2-oxazolyl]methyl]thio]-2-thiazolyl]benzeneacetamide. Acidification with 1 N aqueous HCl gave the hydrochloride salt as a white fluffy solid. HPLC: 98% at 2.54 min (YMC S5 ODS column 4.6×50 mm, 10–90% aqueous methanol over 4 minutes containing 0.2% phosphoric acid, 4 mL/min, monitoring at 220 nm); $[\alpha]_D^{23}=-8.4°$ (c 1.0, methanol).

What is claimed is:

1. A compound of formula I

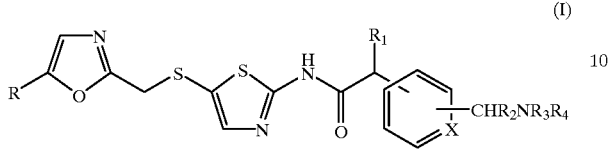

and enantiomers, diastereomers and pharmaceutically acceptable salts thereof wherein R is alkyl;

$R_1$ and $R_2$ are each independently hydrogen or alkyl;

$R_3$ is hydrogen or alkyl, and $R_4$ is hydrogen or alkyl substituted with one or two hydroxy groups or one $NR_5R_6$ group, or $R_3$ and $R_4$ are taken together with the nitrogen atom to which they are attached to form a 4- to 7-membered heterocyclic ring wherein $R_3R_4$ is represented by $—(CH_2)_n—$ where n is an integer of 3, 4, 5 or 6;

$R_5$ and $R_6$ are each independently hydrogen, alkyl, substituted alkyl, cycloalkyl or substituted cycloalkyl, or $R_5$ and $R_6$ are taken together with the nitrogen atom to which they are attached to form a 4- to 7-membered heterocyclic ring wherein $R_5R_6$ is represented by $—(CH_2)_m—$ where m is an integer of 3, 4, 5 or 6; and X is CH or N.

2. The compound according to claim 1 wherein

R is tert-butyl;

$R_1$ and $R_2$ are each independently hydrogen or methyl;

$R_3$ is hydrogen, and $R_4$ is hydrogen, $—CH_2C(CH_3)_2CH_2OH$, $—CH_2CH_2OH$, $—C(CH_3)_2CH_2OH$, $—CH(CH_2OH)_2$, $—CH_2CH(OH)CH_2OH$, $—CH(CH_3)CH_2OH$ or

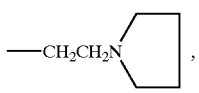

or $R_3$ and $R_4$ are taken together with the nitrogen atom to which they are attached to form a 5-membered heterocyclic ring where $R_3R_4$ is represented by $—(CH_2)_4—$; and X is CH or N.

3. The compound according to claim 1 of formula Ia

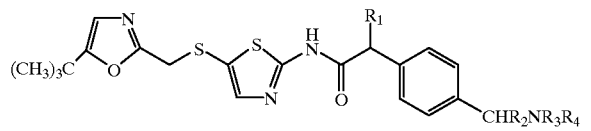

and enantiomers, diastereomers and pharmaceutically acceptable salts thereof wherein $R_1$ and $R_2$ are each independently hydrogen or methyl; and $R_3$ is hydrogen, and $R_4$ is hydrogen, $—CH_2C(CH_3)_2CH_2OH$, $—CH_2CH_2OH$, $—C(CH_3)_2CH_2OH$, $—CH(CH_2OH)_2$, $—CH_2CH(OH)CH_2OH$, $—CH(CH_3)CH_2OH$ or

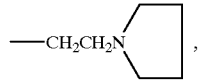

or $R_3$ and $R_4$ are taken together with the nitrogen atom to which they are attached to form a 5-membered heterocyclic ring where $R_3R_4$ is represented by $—(CH_2)_4—$.

4. The compound according to claim 3 of formula Ia wherein $R_1$ and $R_2$ are each independently hydrogen or methyl; and $R_3$ is hydrogen, and $R_4$ is $—CH_2C(CH_3)_2CH_2OH$, $—CH_2CH_2OH$, $—C(CH_3)_2CH_2OH$, $—CH(CH_2OH)_2$, $—CH_2CH(OH)CH_2OH$, $—CH(CH_3)CH_2OH$ or

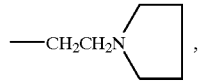

or $R_3$ and $R_4$ are taken together with the nitrogen atom to which they are attached to form a 5-membered heterocyclic ring where $R_3R_4$ is represented by $—(CH_2)_4—$.

5. The compound according to claim 1 of formula Ib

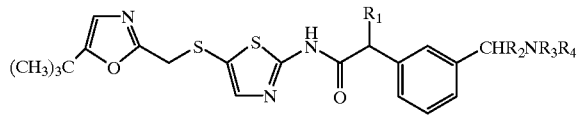

and enantiomers, diastereomers and pharmaceutically acceptable salts thereof wherein $R_1$ and $R_2$ are each independently hydrogen or methyl; and $R_3$ is hydrogen, and $R_4$ is hydrogen, $—CH_2C(CH_3)_2CH_2OH$, $—CH_2CH_2OH$, $—C(CH_3)_2CH_2OH$, $—CH(CH_2OH)_2$, $—CH_2CH(OH)CH_2OH$, $—CH(CH_3)CH_2OH$ or

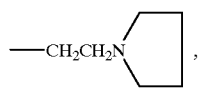

or $R_3$ and $R_4$ are taken together with the nitrogen atom to which they are attached to form a 5-membered heterocyclic ring where $R_3R_4$ is represented by $—(CH_2)_4—$.

6. The compound according to claim 5 of formula Ib wherein $R_1$ and $R_2$ are each independently hydrogen or methyl; and $R_3$ is hydrogen, and $R_4$ is $—CH_2C(CH_3)_2CH_2OH$, $—CH_2CH_2OH$, $—C(CH_3)_2CH_2OH$, $—CH(CH_2OH)_2$, —CH₂CH(OH)CH₂OH, —CH(CH₃)CH₂OH or

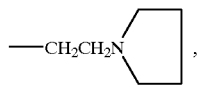

or R₃ and R₄ are taken together with the nitrogen atom to which they are attached to form a 5-membered heterocyclic ring where R₃R₄ is represented by —(CH₂)₄—.

7. The compound according to claim 1 of formula Ic (Ic)

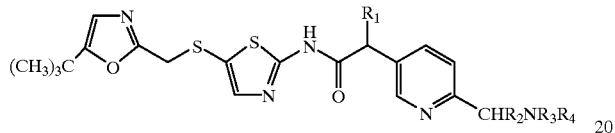

and enantiomers, diastereomers and pharmaceutically acceptable salts thereof wherein R₁ and R₂ are each independently hydrogen or methyl; and R₃ is hydrogen, and R₄ is hydrogen, —CH₂C(CH₃)₂CH₂OH, —CH₂CH₂OH, —C(CH₃)₂CH₂OH, —CH(CH₂OH)₂, —CH₂CH(OH)CH₂OH, —CH(CH₃)CH₂OH or

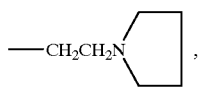

or R₃ and R₄ are taken together with the nitrogen atom to which they are attached to form a 5-membered heterocyclic ring where R₃R₄ is represented by —(CH₂)₄—.

8. The compound according to claim 7 of formula Ic wherein

R₁ and R₂ are each independently hydrogen or methyl; and

R₃ is hydrogen, and R₄ is —CH₂C(CH₃)₂CH₂OH, —CH₂CH₂OH, —C(CH₃)₂CH₂OH, —CH(CH₂OH)₂, —CH₂CH(OH)CH₂OH, —CH(CH₃)CH₂OH or

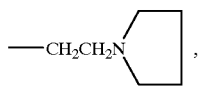

or R₃ and R₄ are taken together with the nitrogen atom to which they are attached to form a 5-membered heterocyclic ring where R₃R₄ is represented by —(CH₂)₄—.

9. The compound according to claim 1 selected from the group consisting of

N-[5-[[[5-(1,1-dimethylethyl)-2-oxazolyl]methyl]thio]-2-thiazolyl]-4-[[[2-hydroxy-1-(hydroxymethyl)ethyl]amino]methyl]benzeneacetamide;

4-[[(2,3-dihydroxypropyl)amino]methyl]-N-[5-[[[5-(1,1-dimethylethyl)-2-oxazolyl]methyl]thio]-2-thiazolyl]benzeneacetamide;

(R)-4-[[(2,3-dihydroxypropyl)amino]methyl]-N-[5-[[[5-(1,1-dimethylethyl)-2-oxazolyl]methyl]thio]-2-thiazolyl]benzeneacetamide;

(S)-4-[[(2,3-dihydroxypropyl)amino]methyl]-N-[5-[[[5-(1,1-dimethylethyl)-2-oxazolyl]methyl]thio]-2-thiazolyl]benzeneacetamide;

4-(aminomethyl)-N-[5-[[[5-(1,1-dimethylethyl)-2-oxazolyl]methyl]thio]-2-thiazolyl]benzeneacetamide;

N-[5-[[[5-(1,1-dimethylethyl)-2-oxazolyl]methyl]thio]-2-thiazolyl]-4-[[(3-hydroxy-2,2-dimethylpropyl)amino]methyl]benzeneacetarnide;

N-[5-[[[5-(1,1-dimethylethyl)-2-oxazolyl]methyl]thio]-2-thiazolyl]-4-(1-pyrrolidinylmethyl)benzeneacetamide;

N-[5-[[[5-(1,1-dimethylethyl)-2-oxazolyl]methyl]thio]-2-thiazolyl]-4-[[(2-hydroxyethyl)amino]methyl]benzeneacetamide;

N-[5-[[[5-(1,1-dimethylethyl)-2-oxazolyl]methyl]thio]-2-thiazolyl]-4-[[[2-(1-pyrrolidinyl)ethyl]amino]methyl]benzeneacetamide;

N-[5-[[[5-(1,1-dimethylethyl)-2-oxazolyl]methyl]thio]-2-thiazolyl]-4-[[(2-hydroxy-1,1-dimethylethyl)amiono]methyl]benzeneacetamide;

N-[5-[[[5-(1,1-dimethylethyl)-2-oxazolyl]methyl]thio]-2-thiazolyl]-3-[[(2-hydroxyethyl)amino]methyl]benzeneacetamide;

N-[5-[[[5-(1,1-dimethylethyl)-2-oxazolyl]methyl]thio]-2-thiazolyl]-3-[[(3-hydroxy-2,2-dimethylpropyl)amino]methyl]benzeneacetamide;

3-(aminomethyl)-N-[5-[[[5-(1,1-dimethylethyl)-2-oxazolyl]methyl]thio]-2-thiazolyl]benzeneacetamide;

N-[5-[[[5-(1,1-dimethylethyl)-2-oxazolyl]methyl]thio]-2-thiazolyl]-4-[[(2-hydroxy-1-methylethyl)amino]methyl]benzeneacetamide;

N-[5-[[[5-(1,1-dimethylethyl)-2-oxazolyl]methyl]thio]-2-thiazolyl]-4-[1-[(2-hydroxyethyl)amino]ethyl]benzeneacetamide;

N-[5-[[[5-(1,1-dimethylethyl)-2-oxazolyl]methyl]thio]-2-thiazolyl]-4-[1-[(2-hydroxy-1-methylethyl)amino]ethyl]benzeneacetamide;

(αS)-N-[5-[[[5-(1,1-dimethylethyl)-2-oxazolyl]methyl]thio]-2-thiazolyl]-4-[[(2-hydroxyethyl)amino]methyl]-α-methylbenzeneacetamide;

N-[5-[[[5-(1,1-dimethylethyl)-2-oxazolyl]methyl]thio]-2-thiazolyl]-6-[[(2-hydroxyethyl)amino]methyl]-3-pyridineacetamide; and N-[5-[[[5-(1,1-dimethylethyl)-2-oxazolyl]methyl]thio]-2-thiazolyl]-4-[[(2-hydroxyethyl)amino]methyl]-α-methylbenzeneacetamide; and pharmaceutically acceptable salts thereof.

10. N-[5-[[[5-(1,1-Dimethylethyl)-2-oxazolyl]methyl]thio]-2-thiazolyl]-4-[[[2-hydroxy-1-(hydroxymethyl)ethyl]amino]methyl]benzeneacetamide and pharmaceutically acceptable salts thereof.

11. N-[5-[[[5-(1,1-Dimethylethyl)-2-oxazolyl]methyl]thio]-2-thiazolyl]-4-[[(2-hydroxy-1,1-dimethylethyl)amino]methyl]benzeneacetamide and pharmaceutically acceptable salts thereof.

12. 4-[[(2,3-Dihydroxypropyl)amino]methyl]-N-[5-[[[5-(1,1-dimethylethyl)-2-oxazolyl]methyl]thio]-2-thiazolyl]benzeneacetamide and pharmaceutically acceptable salts thereof.

13. (R)-4-[[(2,3-Dihydroxypropyl)amino]methyl]-N-[5-[[[5-(1,1-dimethylethyl)-2-oxazolyl]methyl]thio]-2-thiazolyl]benzeneacetamide and pharmaceutically acceptable salts thereof.

14. (S)-4-[[(2,3-Dihydroxypropyl)amino]methyl]-N-[5-[[[5-(1,1-dimethylethyl)-2-oxazolyl]methyl]thio]-2- thiazolyl]benzeneacetamide and pharmaceutically acceptable salts thereof.

15. A pharmaceutical composition which comprises a compound of claim 1 and a pharmaceutically acceptable carrier.

16. A pharmaceutical composition which comprises a compound of claim 1 in combination with a pharmaceutically acceptable carrier and an anti-cancer agent formulated as a fixed dose.

17. A pharmaceutical composition which comprises a compound of claim 1 in combination with a pharmaceutically acceptable carrier and a modulator of p53 transactivation formulated as a fixed dose.

18. A method for modulating apoptosis which comprises administering to a mammalian specie in need thereof an effective apoptosis modulating amount of a compound of claim 1.

19. A method for inhibiting protein kinases which comprises administering to a mammalian specie in need thereof an effective protein kinase inhibiting amount of a compound of claim 1.

20. A method for inhibiting cyclin dependent kinases which comprises administering to a mammalian specie in need thereof an effective cyclin dependent kinase inhibiting amount of a compound of claim 1.

21. A method for inhibiting cdc2 (cdk1) which comprises administering to a mammalian specie in need thereof an effective cdc2 inhibiting amount of a compound of claim 1.

22. A method for inhibiting cdk2 which comprises administering to a mammalian specie in need thereof an effective cdk2 inhibiting amount of a compound of claim 1.

23. A method for inhibiting cdk3 which comprises administering to a mammalian specie in need thereof an effective cdk3 inhibiting amount of a compound of claim 1.

24. A method for inhibiting cdk4 which comprises administering to a mammalian specie in need thereof an effective cdk4 inhibiting amount of a compound of claim 1.

25. A method for inhibiting cdk5 which comprises administering to a mammalian specie in need thereof an effective cdk5 inhibiting amount of a compound of claim 1.

26. A method for inhibiting cdk6 which comprises administering to a mammalian specie in need thereof an effective cdk6 inhibiting amount of a compound of claim 1.

27. A method for inhibiting cdk7 which comprises administering to a mammalian specie in need thereof an effective cdk7 inhibiting amount of a compound of claim 1.

28. A method for inhibiting cdk8 which comprises administering to a mammalian specie in need thereof an effective cdk8 inhibiting amount of a compound of claim 1.

29. A method for treating proliferative diseases which comprises administering to a mammalian specie in need thereof a therapeutically effective amount of a composition of claim 15.

30. A method for treating cancer which comprises administering to a mammalian specie in need thereof a therapeutically effective amount of a composition of claim 15.

31. A method for treating inflammation, inflammatory bowel disease or transplantation rejection which comprises administering to a mammalian specie in need thereof a therapeutically effective amount of a composition of claim 15.

32. A method for treating arthritis which comprises administering to a mammalian specie in need thereof a therapeutically effective amount of a composition of claim 15.

33. A method for treating proliferative diseases which comprises administering to a mammalian specie in need thereof a therapeutically effective amount of a composition of claim 16.

34. A method for treating cancer which comprises administering to a mammalian specie in need thereof a therapeutically effective amount of a composition of claim 16.

35. A method for treating proliferative diseases which comprises administering to a mammalian specie in need thereof a therapeutically effective amount of a composition of claim 17.

36. A method for treating cancer which comprises administering to a mammalian specie in need thereof a therapeutically effective amount of a composition of claim 17.

37. A method for the treatment of a cyclin dependent kinase-associated disorder which comprises administering to a subject in need thereof an amount effective therefor of at least one compound of claim 1.

38. A method for treating chemotherapy-induced alopecia, chemotherapy-induced thrombocytopenia, chemotherapy-induced leukopenia or mucocitis which comprises administering to a mammalian specie in need thereof a therapeutically effective amount of a compound of claim 1.

* * * * *